(12) United States Patent
Choi et al.

(10) Patent No.: US 7,132,422 B2
(45) Date of Patent: Nov. 7, 2006

(54) SODIUM CHANNEL MODULATORS

(75) Inventors: Seok-Ki Choi, Pala Alto, CA (US); Paul R. Fatheree, San Francisco, CA (US); David C. Green, Pacifica, CA (US); Daniel Marquess, Half Moon Bay, CA (US)

(73) Assignee: Theravance, Inc., South San Francisco, CA (US)

( * ) Notice: Subject to any disclaimer, the term of this patent is extended or adjusted under 35 U.S.C. 154(b) by 42 days.

(21) Appl. No.: 11/052,504

(22) Filed: Feb. 4, 2005

(65) Prior Publication Data

US 2005/0130966 A1 Jun. 16, 2005

Related U.S. Application Data

(60) Continuation of application No. 10/659,931, filed on Sep. 11, 2003, now Pat. No. 6,872,741, which is a division of application No. 10/050,696, filed on Jan. 15, 2002, now Pat. No. 6,646,012.

(60) Provisional application No. 60/262,110, filed on Jan. 16, 2001.

(51) Int. Cl.
*A61K 31/5375* (2006.01)
*A61K 31/40* (2006.01)
*C07D 265/30* (2006.01)
*C07D 207/04* (2006.01)

(52) U.S. Cl. ............... 514/237.8; 544/106; 544/162; 546/184; 546/246; 546/329; 546/334; 548/566; 514/231.2; 514/408

(58) Field of Classification Search ............. 544/106, 544/162; 546/184, 246, 329, 334; 548/566; 514/231.2, 237.8, 408
See application file for complete search history.

(56) References Cited

U.S. PATENT DOCUMENTS

| 4,140,779 | A | 2/1979 | Ferland et al. |
| 4,386,090 | A | 5/1983 | Moinet et al. |
| 5,688,830 | A | 11/1997 | Berger et al. |
| 5,985,933 | A | 11/1999 | Zeitlin et al. |
| 6,646,012 | B1 * | 11/2003 | Choi et al. ............. 514/651 |
| 6,756,400 | B1 | 6/2004 | Chinn et al. |
| 6,872,741 | B1 * | 3/2005 | Choi et al. ............. 514/396 |
| 2004/0204460 | A1 | 10/2004 | Chinn et al. |

FOREIGN PATENT DOCUMENTS

| EP | 0 869 119 A1 | 10/1998 |
| FR | 2 496 653 | 6/1982 |
| WO | WO 97/27169 A1 | 7/1997 |

OTHER PUBLICATIONS

De Luca et al., "Molecular Determinants of Mexiletine Structure for Potent and Use-Dependent Block of Skeletal Muscle Sodium Channels", Molecular Pharmacology, vol. 57, pp. 268-277 (2000).
Hunter et al., "Voltage-gated sodium channel blockers for the treatment of chronic pain", Current Opinion in CPNS Investigational Drugs, vol. 1(1), pp. 72-81 (1999).
Loughhead et al., "Synthesis of Mexiletiine Stereoisonomers and Related Compounds via $S_NAr$ Nucleophilic Substitution of a $Cr(CO)_3$-Complexed Aromatic Fluoride", J. Org. Chem., vol. 64, pp. 3373-3375 (1999).
Madge, "Chapter 6. Sodium Channels: Recent Developments and Therapeutic Potential", Annual Reports in Medicinal Chemistry, pp. 51-59 (1998).
Roufos et al., "A Structure-Activity Relationship Study of Novel Phenylacetamides Which Are Sodium Channel Blockers", J. Med. Chem., vol. 39, pp. 1514-1520 (1996).
Zaagama, "β-Adrenoceptor Studies. 5 $^1H$ NMR and IR Spectroscopic Analysis of the Conformation of the Hydrohalide Salts of β-Adrenoceptor-Blocking Aryloxypropanolamines. Evidence for a Seven-Membered Ring Structure with Participation of Two Hydrogen Bonds", J. Med. Chem., vol. 22, No. 4, pp. 441-449 (1979).

* cited by examiner

*Primary Examiner*—Golam M. M. Shameem
(74) *Attorney, Agent, or Firm*—Jeffrey A. Hagenah

(57) ABSTRACT

The invention provides sodium channel modulating compounds which are useful for treating diseases or conditions associated with sodium channel activity, such as neuropathic pain. The invention also provides pharmaceutical compositions comprising a compound of the present invention, as well as therapeutic methods comprising administering such a compound or salt to a mammal (e.g. a human).

11 Claims, No Drawings

SODIUM CHANNEL MODULATORS

CROSS-REFERENCE TO RELATED APPLICATIONS

This application is a continuation of U.S. Ser. No. 10/659,931, filed 11 Sep. 2003 now U.S. Pat. No. 6,872,741, which is a divisional application Ser. No. 10/050,696 of U.S. Pat. No. 6,646,012, filed 15 Jan. 2002; which claims priority from U.S. Provisional Application No. 60/262,110, filed 16 Jan. 2001.

FIELD OF THE INVENTION

The invention is directed to novel compounds that bind to sodium channels and modulate their activity. The invention is also directed to pharmaceutical compositions comprising such compounds, methods of using such compounds to treat diseases associated with the activity of sodium channels, and processes and intermediates useful for preparing such compounds.

BACKGROUND

Voltage-gated ion channels play a critical role in the electrical activity of neuronal and muscle cells. Large families of voltage-gated ion channels (e.g. sodium channels) have been identified. These ion channels have been the target of significant pharmacologic study, due to their potential role in a variety of pathological conditions.

For example, the activity of sodium channels has been implicated in numerous pathological conditions, including neuropathic pain. Neuropathic pain is a chronic condition associated with diabetes, chronic inflammation, cancer and herpes virus infection. An estimated 75 million people worldwide are expected to suffer from neuropathic pain by the year 2010. Unfortunately, current treatment options typically provide only partial pain relief, and are limited by inconvenient dosing and by side effects, such as somnolence, ataxia, edema, gastrointestinal discomfort and respiratory depression.

Thus, despite the limited success that has been achieved using sodium channel modulators to treat pain, there continues to be a need for novel agents and methods that are useful for treating neuropathic pain, as well as other conditions associated with the activity of sodium channels. Particularly useful agents may be more potent or cause fewer side effects than existing agents.

SUMMARY OF THE INVENTION

The present invention provides novel compounds that modulate (e.g. block) sodium channel activity. Accordingly, the invention provides a compound of the invention, which is a compound of formula (I):

$$R_1\text{—}O\text{—}R_2\text{—}X\text{—}R_3 \quad (I)$$

wherein
$R_1$ is aryl;
$R_2$ is a group of formula (II):

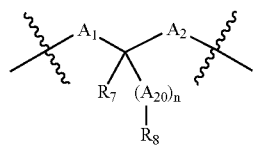

(II)

wherein:
$A_1$, $A_2$, and $A_{20}$ are each independently alkylene or substituted alkylene;
n is 0 or 1;
$R_7$ is hydrogen, alkyl, or substituted alkyl; and
$R_8$ is $NR_{10}R_{11}$, wherein each of $R_{10}$ and $R_{11}$ is independently hydrogen, alkyl, or substituted alkyl; and
X is oxygen and $R_3$ is aryl, heteroaryl, cycloalkyl, substituted cycloalkyl, heterocycle, alkyl, or substituted alkyl; or
X is a direct bond and $R_3$ is an N-linked heteroaryl or an N-linked heterocycle;
wherein any aryl of $R_1$–$R_3$ can optionally be substituted with from 1 to 5 substituents $R_g$; wherein each $R_g$ is independently selected from the group consisting of hydroxy, alkyl, substituted alkyl, alkoxy, cycloalkoxy, substituted cycloalkoxy, methanediol (—OCH$_2$O—), ethanediol (—OCH$_2$CH$_2$O—), cycloalkyl, substituted alkyl, substituted alkoxy, substituted cycloalkyl, amino, substituted amino, aryl, aryloxy, carboxy, carboxylalkyl (e.g. —CO$_2$Me), carboxyl(substituted alkyl) (e.g. —CO$_2$(substituted alkyl)), cyano, halo, nitro, heteroaryl, heteroaryloxy, heterocyclic, heterocylooxy, heteroaryl and trihalomethyl;

and wherein any heteroaryl of $R_2$–$R_3$ can be optionally substituted with 1 to 5 substituents $R_h$, wherein each $R_h$ is independently selected from the group consisting of hydroxy, alkyl, alkoxy, substituted alkoxy, cycloalkoxy, substituted cycloalkoxy, substituted alkyl, arylalkyl, heteroarylalkyl, heterocyclealkyl, substituted cycloalkyl, amino, substituted amino, aryl, aryloxy, carboxyl (—COOH), carboxylalkyl (e.g. —CO$_2$Me), carboxyl(substituted alkyl), cyano, halo, nitro, heterocyclic, and trihalomethyl.

or a pharmaceutically acceptable salt thereof.

A preferred compound of formula (I) is a compound of formula (III):

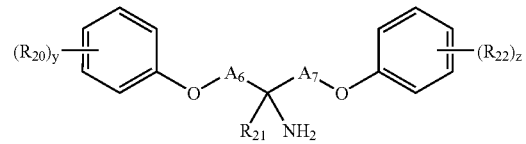

(III)

wherein:
$A_6$ and $A_7$ are each independently alkylene or substituted alkylene;
each $R_{20}$ is independently halo, alkyl, substituted alkyl, aryl, alkoxy, substituted alkoxy, cycloalkoxy, substituted cycloalkoxy, trifluoromethyl, cyano, nitro, hydroxy, $NR_4R_5$, or $CO_2R_6$;
$R_{21}$ is hydrogen, alkyl, or substituted alkyl;
each $R_{22}$ is independently halo, alkyl, substituted alkyl, aryl, heteroaryl, cycloalkyl, substituted cycloalkyl, heterocycle, alkoxy, substituted alkoxy, cycloalkoxy, substituted cycloalkoxy, trifluoromethyl, cyano, nitro, hydroxy, $NR_4R_5$, or $CO_2R_6$;
y is 0, 1, 2, 3, 4, or 5;
z is 0, 1, 2, 3, 4, or 5; and
$R_4$–$R_6$ are each independently hydrogen, alkyl, or substituted alkyl;
wherein any aryl of $A_6$, $A_7$, $R_{20}$–$R_{22}$ and $R_4$–$R_6$ can optionally be substituted with from 1 to 5 substituents $R_g$; wherein each $R_g$ is independently selected from the group consisting of hydroxy, alkyl, substituted alkyl, alkoxy, cycloalkoxy, substituted cycloalkoxy, methanediol (—OCH₂O—), ethanediol (—OCH₂CH₂O—), cycloalkyl, substituted alkyl, substituted alkoxy, substituted cycloalkyl, amino, substituted amino, aryl, aryloxy, carboxy, carboxylalkyl (e.g. —CO₂Me), carboxyl(substituted alkyl), cyano, halo, nitro, heteroaryl, heteroaryloxy, heterocyclic, heterocyclooxy, heteroaryl and trihalomethyl;

and wherein any heteroaryl of $A_6$, $A_7$, $R_{20}$–$R_{22}$ and $R_4$–$R_6$ can be optionally substituted with 1 to 5 substituents $R_h$, wherein each $R_h$ is independently selected from the group consisting of hydroxy, alkyl, alkoxy, substituted alkoxy, cycloalkoxy, substituted cycloalkoxy, substituted alkyl, arylalkyl, heteroarylalkyl, heterocyclealkyl, substituted cycloalkyl, amino, substituted amino, aryl, aryloxy, carboxyl (—COOH), carboxylalkyl (e.g. —CO₂Me), carboxyl(substituted alkyl), cyano, halo, nitro, heterocyclic, and trihalomethyl.

or a pharmaceutically acceptable salt thereof.

Another preferred compound of formula (I) is a compound of formula (IV):

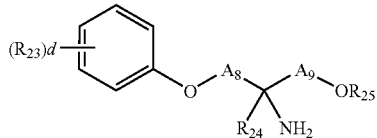

(IV)

wherein:

$A_8$ and $A_9$ are each independently alkylene or substituted alkylene;

each $R_{23}$ is independently halo, alkyl, substituted alkyl, aryl, heteroaryl, cycloalkyl, substituted cycloalkyl, heterocycle, alkoxy, substituted alkoxy, cycloalkoxy, substituted cycloalkoxy, trifluoromethyl, cyano, nitro, hydroxy, $NR_4R_5$, or $CO_2R_6$;

$R_{24}$ is hydrogen, alkyl, or substituted alkyl;

$R_{25}$ is alkyl, substituted alkyl, aryl, heteroaryl, cycloalkyl, substituted cycloalkyl, or heterocycle;

d is 0, 1, 2, 3, 4, or 5; and $R_4$–$R_6$ are each independently hydrogen, alkyl, or substituted alkyl;

wherein any aryl of $A_8$, $A_9$, $R_{23}$–$R_{25}$ and $R_4$–$R_6$ can optionally be substituted with from 1 to 5 substituents $R_g$; wherein each $R_g$ is independently selected from the group consisting of hydroxy, alkyl, substituted alkyl, alkoxy, cycloalkoxy, substituted cycloalkoxy, methanediol (—OCH₂O—), ethanediol (—OCH₂CH₂O—), cycloalkyl, substituted alkyl, substituted alkoxy, substituted cycloalkyl, amino, substituted amino, aryl, aryloxy, carboxy, carboxylalkyl (e.g. —CO₂Me), carboxyl(substituted alkyl), cyano, halo, nitro, heteroaryl, heteroaryloxy, heterocyclic, heterocyclooxy, heteroaryl and trihalomethyl;

and wherein any heteroaryl of $A_8$, $A_9$, $R_{23}$–$R_{25}$ and $R_4$–$R_6$ can be optionally substituted with 1 to 5 substituents $R_h$, wherein each $R_h$ is independently selected from the group consisting of hydroxy, alkyl, alkoxy, substituted alkoxy, cycloalkoxy, substituted cycloalkoxy, substituted alkyl, arylalkyl, heteroarylalkyl, heterocyclealkyl, substituted cycloalkyl, amino, substituted amino, aryl, aryloxy, carboxyl (—COOH), carboxylalkyl (e.g. —CO₂Me), carboxyl(substituted alkyl), cyano, halo, nitro, heterocyclic, and trihalomethyl.

or a pharmaceutically acceptable salt thereof.

Another preferred compound of formula (I) is a compound of formula (V):

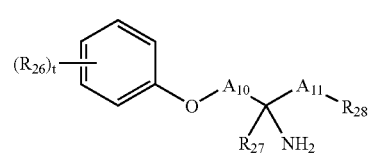

(V)

wherein:

$A_{10}$ and $A_{11}$ are each independently alkylene or substituted alkylene;

each $R_{26}$ is independently halo, alkyl, substituted alkyl, aryl, heteroaryl, cycloalkyl, substituted cycloalkyl, heterocycle, alkoxy, substituted alkoxy, cycloalkoxy, substituted cycloalkoxy, trifluoromethyl, cyano, nitro, hydroxy, $NR_4R_5$, or $CO_2R_6$;

$R_{27}$ is hydrogen, alkyl, or substituted alkyl;

$R_{28}$ is an N-linked heteroaryl or an N-linked heterocycle;

t is 0, 1, 2, 3, 4, or 5; and $R_4$–$R_6$ are each independently hydrogen, alkyl, or substituted alkyl;

wherein any aryl of $A_{10}$, $A_{11}$, $R_{26}$–$R_{28}$ and $R_4$–$R_6$ can optionally be substituted with from 1 to 5 substituents $R_g$; wherein each $R_g$ is independently selected from the group consisting of hydroxy, alkyl, substituted alkyl, alkoxy, cycloalkoxy, substituted cycloalkoxy, methanediol (—OCH₂O—), ethanediol (—OCH₂CH₂O—), cycloalkyl, substituted alkyl, substituted alkoxy, substituted cycloalkyl, amino, substituted amino, aryl, aryloxy, carboxy, carboxylalkyl (e.g. —CO₂Me), carboxyl(substituted alkyl), cyano, halo, nitro, heteroaryl, heteroaryloxy, heterocyclic, heterocyclooxy, heteroaryl and trihalomethyl;

and wherein any heteroaryl of $A_{10}$, $A_{11}$, $R_{26}$–$R_{28}$ and $R_4$–$R_6$ can be optionally substituted with 1 to 5 substituents $R_h$, wherein each $R_h$ is independently selected from the group consisting of hydroxy, alkyl, alkoxy, substituted alkoxy, cycloalkoxy, substituted cycloalkoxy, substituted alkyl, arylalkyl, heteroarylalkyl, heterocyclealkyl, substituted cycloalkyl, amino, substituted amino, aryl, aryloxy, carboxyl (—COOH), carboxylalkyl (e.g. —CO₂Me), carboxyl(substituted alkyl), cyano, halo, nitro, heterocyclic, and trihalomethyl.

or a pharmaceutically acceptable salt thereof.

Another preferred compound of formula (I) is a compound of formula (VI):

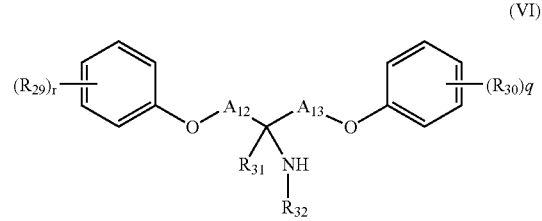

(VI)

wherein:

$A_{12}$ and $A_{13}$ are each independently alkylene or substituted alkylene;

each $R_{29}$ is independently halo, alkyl, substituted alkyl, aryl, heteroaryl, cycloalkyl, substituted cycloalkyl, heterocycle, alkoxy, substituted alkoxy, cycloalkoxy, substituted cycloalkoxy, trifluoromethyl, cyano, nitro, hydroxy, $NR_4R_5$, or $CO_2R_6$;

each $R_{30}$ is independently halo, alkyl, substituted alkyl, aryl, heteroaryl, cycloalkyl, substituted cycloalkyl, heterocycle, alkoxy, substituted alkoxy, cycloalkoxy, substituted cycloalkoxy, trifluoromethyl, cyano, nitro, hydroxy, $NR_4R_5$, or $CO_2R_6$;

$R_{31}$ is hydrogen, alkyl, or substituted alkyl;

$R_{32}$ is alkyl, substituted alkyl, aryl, heteroaryl, cycloalkyl, substituted cycloalkyl, or heterocycle;

r is 0, 1, 2, 3, 4, or 5;

q is 0, 1, 2, 3, 4, or 5; and $R_4$–$R_6$ are each independently hydrogen, alkyl, or substituted alkyl;

wherein any aryl of $A_{12}$, $A_{13}$, $R_{29}$–$R_{32}$ and $R_4$–$R_6$ can optionally be substituted with from 1 to 5 substituents $R_g$; wherein each $R_g$ is independently selected from the group consisting of hydroxy, alkyl, substituted alkyl alkoxy, cycloalkoxy, substituted cycloalkoxy, methanediol (—$OCH_2O$—), ethanediol (—$OCH_2CH_2O$—), cycloalkyl, substituted alkyl, substituted alkoxy, substituted cycloalkyl, amino, substituted amino, aryl, aryloxy, carboxy, carboxylalkyl (e.g. —$CO_2Me$), carboxyl(substituted alkyl), cyano, halo, nitro, heteroaryl, heteroaryloxy, heterocyclic, heterocyclooxy, heteroaryl and trihalomethyl;

and wherein any heteroaryl of $A_{12}$, $A_{13}$, $R_{29}$–$R_{32}$ and $R_4$–$R_6$ can be optionally substituted with 1 to 5 substituents $R_h$, wherein each $R_h$ is independently selected from the group consisting of hydroxy, alkyl, alkoxy, substituted alkoxy, cycloalkoxy, substituted cycloalkoxy, substituted alkyl, arylalkyl, heteroarylalkyl, heterocyclealkyl, substituted cycloalkyl, amino, substituted amino, aryl, aryloxy, carboxyl (—COOH), carboxylalkyl (e.g. —$CO_2Me$), carboxyl(substituted alkyl), cyano, halo, nitro, heterocyclic, and trihalomethyl.

or a pharmaceutically acceptable salt thereof.

The invention also provides a pharmaceutical composition comprising a compound of the invention and pharmaceutically acceptable carrier.

The invention also provides a method of treating a disease or condition associated with sodium channel activity (e.g. neuropathic pain) in a mammal, comprising administering to the mammal, a therapeutically effective amount of a compound of the invention. The invention also provides a method of treating a disease or condition associated with sodium channel activity (e.g. neuropathic pain) in a mammal, comprising administering to the mammal, a therapeutically effective amount of a pharmaceutical composition of the invention.

The invention also provides processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with sodium channel activity (e.g. neuropathic pain) in a mammal.

Preferred compounds of the invention are the compounds of formulas I and III–VI shown in Tables I–XI below.

TABLE IV
Preferred Compounds of Formula I
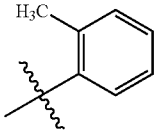
| Compound | R₁ | R₃ |
|---|---|---|
| 7 | 2,6-dimethylphenyl | 2,6-dimethylphenyl |
| 8 | 2-methylphenyl | 2-methylphenyl |
| 9 | 2,4-dimethylphenyl | 2,4-dimethylphenyl |
TABLE V
Preferred Compounds of Formula I
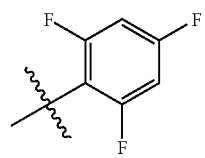
| Compound | R₃ |
|---|---|
| 10 | 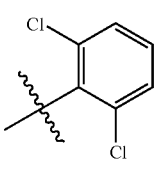 |
| 11 | 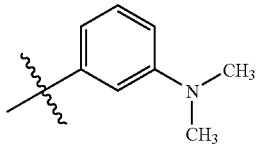 |
| 12 | 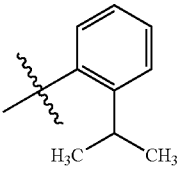 |
| 13 | 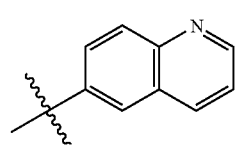 |
| 14 | 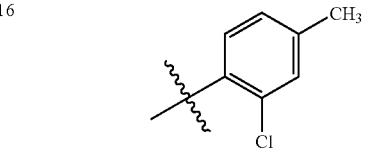 |
| 15 | 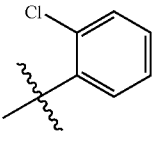 |
TABLE V-continued
Preferred Compounds of Formula I
| Compound | R₃ |
|---|---|
| 16 | 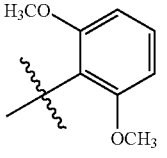 |
| 17 | 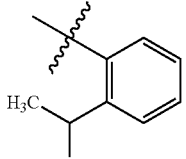 |
TABLE VI
Preferred Compounds of Formula I
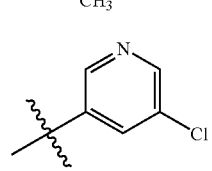
| Compound | R₃ |
|---|---|
| 18 | |
| 19 | |
| 20 | |
| 21 | |

TABLE VI-continued

Preferred Compounds of Formula I

[Structure: 2-methylphenoxy group connected to CH2-C(CH3)(NH2)-CH2-O-R3]

| Compound | R3 |
|---|---|
| 22 | 2-methoxyphenyl |
| 23 | 2-(trifluoromethyl)phenyl |
| 24 | 2-cyanophenyl |
| 25 | 6-methylpyridin-3-yl |
| 26 | 5,6,7,8-tetrahydronaphthalen-1-yl |
| 27 | quinolin-6-yl |
| 28 | 3,5-bis(trifluoromethyl)phenyl |
| 29 | 4-cyano-2-methoxyphenyl |

TABLE VII

Preferred Compounds of Formula I

[Structure: 2,6-dimethylphenoxy group connected to CH2-CH(NH2)-CH2-R3]

| Compound | R3 |
|---|---|
| 30 | imidazol-1-yl |
| 31 | 3,5-dimethylpyrazol-1-yl |
| 32 | 2-phenylimidazol-1-yl |
| 33 | 2-ethylimidazol-1-yl |
| 34 | 4-phenylimidazol-1-yl |
| 35 | benzimidazol-1-yl |
| 36 | 4-(methoxycarbonyl)imidazol-1-yl |
| 37 | —O—CH2—cyclopentyl |
| 38 | —O—CH2CH2CH2—N(CH3)2 |

TABLE VII-continued
Preferred Compounds of Formula I

| Compound | R₃ |
|---|---|
| 39 | *tert*-butoxy group |
| 40 | 2-biphenylmethoxy group |
| 41 | 4-butoxybenzyloxy group |
| 42 | 2-(thiophen-2-yl)ethoxy group |
| 43 | 3-ethoxypropoxy group |
| 44 | 3-phenylpropoxy group |
| 45 | 2-(4-(dimethylamino)phenyl)ethoxy group |
| 46 | 2-(pyridin-4-yl)ethoxy group |

TABLE VIII
Preferred Compounds of Formula I

| Compound | R₃ |
|---|---|
| 47 | 3,5-dimethylpyrazol-1-yl group |
| 48 | 2-phenylimidazol-1-yl group |
| 49 | 2-ethylimidazol-1-yl group |
| 50 | 2-ethyl-4-methylimidazol-1-yl group |
| 51 | 4-phenylimidazol-1-yl group |
| 52 | benzimidazol-1-yl group |
| 53 | 4-(methoxycarbonyl)imidazol-1-yl group |
| 54 | 3-ethoxypropoxy group |
| 55 | 3-phenylpropoxy group |

TABLE VIII-continued
Preferred Compounds of Formula I
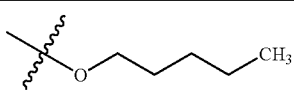
| Compound | R₃ |
|---|---|
| 56 | 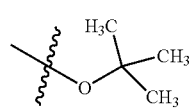 |
| 57 | 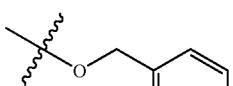 |
| 58 | 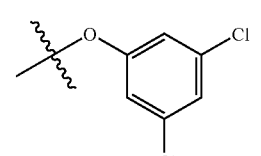 |
| 59 | 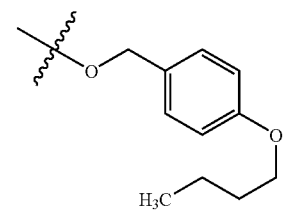 |
| 60 | 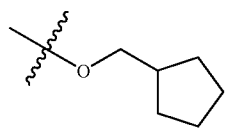 |
| 61 | 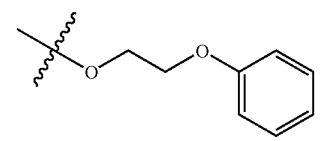 |
| 62 | 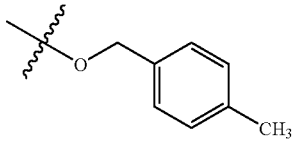 |
| 63 | 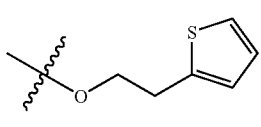 |
| 64 | 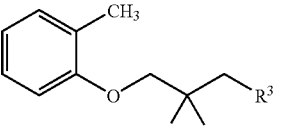 |
| 65 | 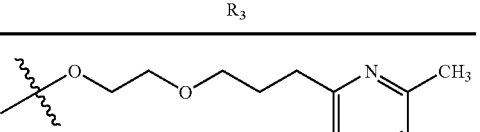 |
| 66 | |
| 67 | |
| 68 | |
| 69 | |
| 70 | |
| 71 | |
| 72 | |
| 73 | |

TABLE VIII-continued
Preferred Compounds of Formula I
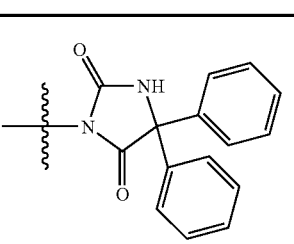
| Compound | R₃ |
|---|---|
| 92 | 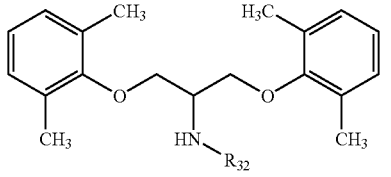 |
TABLE IX
Preferred Compounds of Formula VI
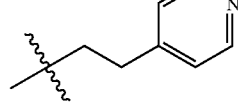
| Compound | R₃₂ |
|---|---|
| 74 | 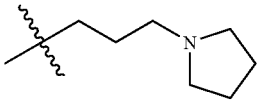 |
| 75 | 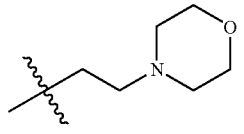 |
| 76 | 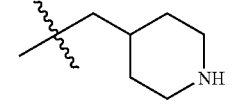 |
| 77 | 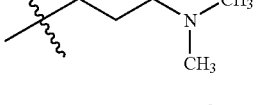 |
| 78 | 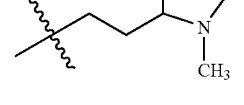 |
TABLE IX-continued
Preferred Compounds of Formula VI
| Compound | R₃₂ |
|---|---|
| 79 | 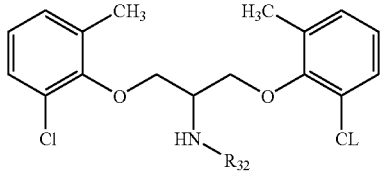 |
| 80 | 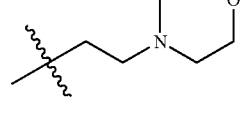 |
TABLE X
Preferred Compounds of Formula VI
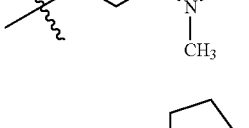
| Compound | R₃₂ |
|---|---|
| 81 | 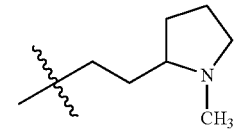 |
| 82 | |
| 83 | |
| 84 | |

TABLE XI

Preferred Compounds of Formula VI

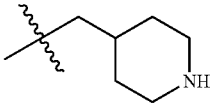

| Compound | R$_{32}$ |
|---|---|
| 85 | 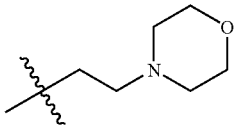 |
| 86 | 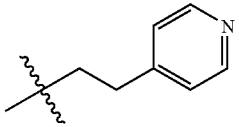 |
| 87 | 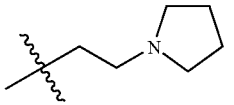 |
| 88 | 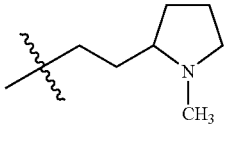 |
| 89 | 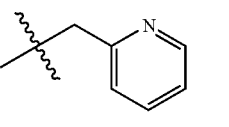 |
| 90 | 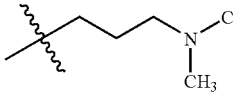 |
| 91 |  |

DETAILED DESCRIPTION OF THE INVENTION

The following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, -butyl, iso-butyl, n-hexyl, n-decyl, tetradecyl, and the like.

The term "substituted alkyl" refers to an alkyl group as defined above wherein one or more carbon atoms in the alkyl chain have been replaced with a heteroatom such as —O—, —NR— (where R is hydrogen or alkyl), or —NRR— (where each R is independently hydrogen or alkyl) and/or wherein the alkyl group is substituted with from 1 to 5 substituents selected from the group consisting of cycloalkyl, substituted cycloalkyl, carboxylalkyl (e.g. —CO$_2$Me), carboxyl(substituted alkyl), cyano, halogen, hydroxyl, keto (═O), carboxyl (COOH), aryl, aryloxy, heteroaryl, heteroaryloxy, heterocyclic, heterocyclooxy, nitro, and —NR$^a$R$^b$, wherein R$^a$ and R$^b$ may be the same or different and are chosen from hydrogen, alkyl, arylalkyl, heteroarylalkyl, heterocyclealkyl, cycloalkyl, substituted cycloalkyl, aryl, heteroaryl and heterocyclic. This term is exemplified by groups such as hydroxymethyl, hydroxyethyl, hydroxypropyl, 2-aminoethyl, 3-aminopropyl, 2-methylaminoethyl, 3-dimethylaminopropyl, 2-carboxyethyl, and the like.

The term "alkylene" refers to a diradical of a branched or unbranched saturated hydrocarbon chain, preferably having from 1 to 10 carbon atoms, more preferably 1 to 6 carbon atoms and even more preferably 1 to 3 carbon atoms. This term is exemplified by groups such as methylene (—CH$_2$—), the propylene isomers (e.g., —CH$_2$CH$_2$CH$_2$— and —CH(CH$_3$)CH$_2$—), ethylene (—CH$_2$CH$_2$—), 1,1-ethanediyl (—CH(CH$_3$)—), and the like.

The term "substituted alkylene" refers to an alkylene group, as defined above, wherein the chain is interrupted with one or more non-peroxide oxy (—O—) and/or wherein the alkyl group is substituted with from 1 to 5 substituents, and preferably 1 to 3 substituents, selected from the group consisting of cycloalkyl, substituted cycloalkyl, amino, substituted amino, cyano, halogen, hydroxy, keto (═O), carboxyl, carboxylalkyl, carboxyl(substituted alkyl), aryl, aryloxy, heteroaryl, heteroaryloxy, heterocyclic, heterocyclooxy, hydroxyamino, alkoxyamino, and nitro. Additionally, such substituted alkylene groups include those where 2 substituents on the alkylene group are fused to form one or more cycloalkyl, substituted cycloalkyl, aryl, heterocyclic or heteroaryl groups fused to the alkylene group. Preferably such fused groups contain from 1 to 3 fused ring structures.

The term "alkoxy" refers to the groups alkyl-O—, where alkyl is as defined herein. Preferred alkoxy groups include, by way of example, methoxy, ethoxy, -propoxy, iso-propoxy, n-butoxy, tert-butoxy, sec-butoxy, n-pentoxy, n-hexoxy, 1,2-dimethylbutoxy, and the like.

The term "substituted alkoxy" refers to the group (substituted alkyl)-O—, where substituted alkyl is as defined herein.

The term "aryl" refers to a monovalent unsaturated aromatic carbocyclic group which may be monocyclic or multicyclic (i.e., fused). Such aryl groups preferably contain from 6 to 20 carbon atoms; more preferably, from 6 to 10 carbon atoms. This term also includes aryl groups fused to a cycloalkyl, heteroaryl, or heterocyclyl group in which the point of attachment is on the aromatic (aryl) portion of the group. Representative aryl groups include, by way of example, phenyl, naphthyl, azulenyl, indan-5-yl, 1,2,3,4-tetrahydronaphth-6-yl, 2,3-dihydrobenzofuran-5-yl and the like. Preferred aryl substituents R$_g$ include alkyl, methanediol, ethanediol, alkoxy, halo, cyano, nitro, and trihalomethyl.

The term "aryloxy" refers to the group aryl-O— wherein the aryl group is as defined above including optionally substituted aryl groups as also defined above.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, aryl, heteroaryl, and heterocyclic provided that both R's are not hydrogen.

The term "hydroxamino" refers to the group —NR$^c$R$^d$, wherein R$^c$ is hydroxy and each R$^d$ is independently hydrogen or alkyl.

The term "alkoxamino" refers to the group —NR$^e$R$^f$, wherein R$^e$ is alkoxy and R$^f$ is hydrogen or alkyl.

The term "cycloalkyl" refers to alkyl groups of from 3 to 20 carbon atoms comprising a single carbocyclic ring or multiple condensed carbocyclic rings. Such cycloalkyl groups include, by way of example, single ring structures such as cyclopropyl, methylcyclopropyl, cyclobutyl, cyclopentyl, dimethylcyclopentyl, cyclohexyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkyl, alkoxy, substituted alkoxy, cycloalkoxy, substituted cycloalkoxy, cycloalkyl, amino, substituted amino, cyano, halogen, hydroxy, keto, carboxy, carboxylalkyl (e.g. —CO$_2$Me), carboxyl(substituted alkyl), aryl, aryloxy, heteroaryl, heteroaryloxy, heterocyclic, hydroxyamino, and nitro.

The term "cycloalkoxy" refers to the group cycloalkyl-O—, where cycloalkyl is as defined herein. Preferred cycloalkoxy groups include, by way of example, cyclopentyloxy and cyclohexyloxy, and the like.

The term "substituted cycloalkoxy" refers to the group (substituted cycloalkyl)-O—, where substituted cycloalkyl is as defined herein.

The term "halo" refers to fluoro, chloro, bromo and iodo.

The term "trihalomethyl" includes trifluoromethyl and trichloromethyl.

The term "heteroaryl" refers to a monovalent aromatic group which contains at least one heteroatom, preferably 1 to 4 heteroatoms, selected from N, S and O within at least one aromatic ring and which may be monocyclic or multicyclic (i.e., fused). Such heteroaryl groups preferably contain from 5 to 20 atoms; more preferably, from 5 to 10 atoms. This term also include such a heteroaryl group fused to a cycloalkyl, aryl, or heterocyclyl group, provided the point of attachment is on a heteroatom-containing aromatic ring. Representative heteroaryl groups include, by way of example, pyrroyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, quinolyl, indolyl, isoquinolyl and the like. Preferred heteroaryl substituents R$_h$ include alkyl, alkoxy, halo, cyano, nitro, and trihalomethyl.

The term "heterocycle" refers to a monovalent saturated or partially unsaturated cyclic non-aromatic group which contains at least one heteroatom, preferably 1 to 4 heteroatoms, selected from nitrogen (NR$_x$, wherein R$_x$ is hydrogen, alkyl, or a direct bond at the point of attachment of the heterocycle group), sulfur, phosphorus, and oxygen within at least one cyclic ring and which may be monocyclic or multicyclic. Such heterocycle groups preferably contain from 3 to 20 atoms; more preferably, from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2, 3,4-tetrahydroisoquinolin-2-yl, quinuclidinyl and the like. Unless otherwise constrained by the definition for heterocycle, such heterocycle groups can be optionally substituted with 1 to 5, and preferably 1 to 3 substituents, selected from the group consisting of alkyl, alkoxy, substituted alkoxy, cycloalkoxy, substituted cycloalkoxy, cycloalkyl, substituted cycloalkyl, amino, substituted amino, cyano, halogen, hydroxyl, keto, carboxyl, carboxylalkyl (e.g. —CO$_2$Me), carboxyl(substituted alkyl), aryl, aryloxy, heteroaryl, hydroxyamino, and nitro. Such heterocyclic groups can have a single ring or multiple condensed rings. Preferred heterocyclics include morpholino, piperidinyl, and the like.

The term "heteroarylalkyl" refers to an alkyl group as defined herein, which is substituted with from 1 to 5 (preferably 1) heteroaryl groups. Such groups are exemplified by pyridylmethyl, pyridylethyl, indolylmethyl, and the like.

The term "arylalkyl" refers to an alkyl group as defined herein, which is substituted with from 1 to 5 (preferably 1) aryl groups. Such groups are exemplified by benzyl, phenethyl, and 3-phenylpropyl.

The term "heterocyclealkyl" refers to an alkyl group as defined herein, which is substituted with from 1 to 5 (preferably 1) heterocycle groups. Such groups are exemplified by piperidinomethyl, morpholinomethyl, morpholinoethyl, piperidinomethyl, 4-morphilinylmethyl, and 2-(4-morpholinyl)ethyl, and the like.

Examples of nitrogen heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxynitrogen containing heterocycles.

The term "N-linked heteroaryl" refers to a heteroaryl, as defined herein, which is linked to the remaining portion of the molecule through a nitrogen atom of an aromatic ring.

The term "N-linked heterocycle" refers to a heterocycle, as defined herein, which is linked to the remaining portion of the molecule through a nitrogen atom of a non-aromatic heteroatom-containing ring.

As to any group defined herein which contains one or more substituents, it is understood, of course, that such groups do not contain any substitution or substitution patterns which are sterically impractical, synthetically non-feasible and/or sufficiently liable to have no utility. In addition, the compounds of this invention include all stereochemical isomers arising from the substitution of these compounds.

Unless specified otherwise, all ranges referred to herein include the stated end-point values.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human) which includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The phrase "disease or condition associated with sodium channel activity" includes all disease states and/or conditions that are acknowledged now, or that are found in the future, to be associated with the activity of sodium channels. Such disease states include, but are not limited to, pathophysiological disorders, including hypertension, cardiac arrhythmogenesis, insulin-dependent diabetes, non-insulin dependent diabetes mellitus, diabetic neuropathy, seizures, tachycardia, ischemic heart disease, cardiac failure, angina, myocardial infarction, transplant rejection, autoimmune disease, sickle cell anemia, muscular dystrophy, gastrointestinal disease, mental disorder, sleep disorder, anxiety disorder, eating disorder, neurosis, alcoholism, inflammation, cerebrovascular ischemia, CNS diseases, epilepsy, Parkinson's disease, asthma, incontinence, urinary dysfunction, micturition disorder, irritable bowel syndrome, restenosis, subarachnoid hemorrhage, Alzheimer disease, drug dependence/addiction, schizophrenia, Huntington's chorea, tension-type headache, trigeminal neuralgia, cluster headache, migraine (acute and prophylaxis), inflammatory pain, neuropathic pain and depression.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of the invention may contain one or more chiral centers. Accordingly, the invention includes racemic mixtures, diastereomers, enantiomers and mixture enriched in one or more steroisomer. The scope of the invention as described and claimed encompasses the racemic forms of the compounds as well as the individual enantiomers and non-racemic mixtures thereof.

Specific and preferred values listed below for radicals, substituents, and ranges, are for illustration only, they do not exclude other defined values or other values within defined ranges for the radicals and substituents.

Specifically, $R_1$ can be aryl optionally substituted with one or more halo or alkyl.

Specifically, $R_1$ can be phenyl optionally substituted with about 1 to about 3 halo and/or alkyl.

Specifically, halo can be fluoro or chloro.

Specifically, alkyl can be methyl.

Specifically, aryl can be phenyl.

Specifically, $R_1$ is 2-methylphenyl, 2-chloro-6-methylphenyl, 2,4,6-trifluorophenyl, 2,6-dimethylphenyl, or 2,4-dimethylphenyl.

Specifically, $A_1$–$A_{13}$ and $A_{20}$ can be alkylene or substituted alkylene having from about 1 to about 6 carbon atoms.

Specifically, $A_1$–$A_{13}$ and $A_{20}$ can be alkylene or substituted alkylene having from about 1 to about 3 carbon atoms.

Specifically, $A_1$ can be methylene or 1,1-ethanediyl.

Specifically, $A_2$ can be methylene.

Specifically, $R_7$ can be hydrogen.

Specifically, $R_7$ can be methyl.

Specifically, $R_9$ can be amino.

Specifically, n can be 0.

Specifically, $R_{10}$ can be hydrogen.

Specifically, $R_{11}$ can be hydrogen.

Specifically, $R_{11}$ can be heterocyclealkyl, heteroarylalkyl, or alkyl.

Specifically, $R_{11}$ is 2-morpholinoethyl, 2-(pyrrolidin-1-yl)ethyl, 4-piperidinylmethyl, 3-(N,N-dimethylamino)propyl, 2-(1-methyl-pyrrolidin-2-yl)ethyl, 2-(4-pyridyl)ethyl, or 3-(1-pyrrolidin-1-yl)propyl.

Specifically, $R_2$ can be a group of the formula:

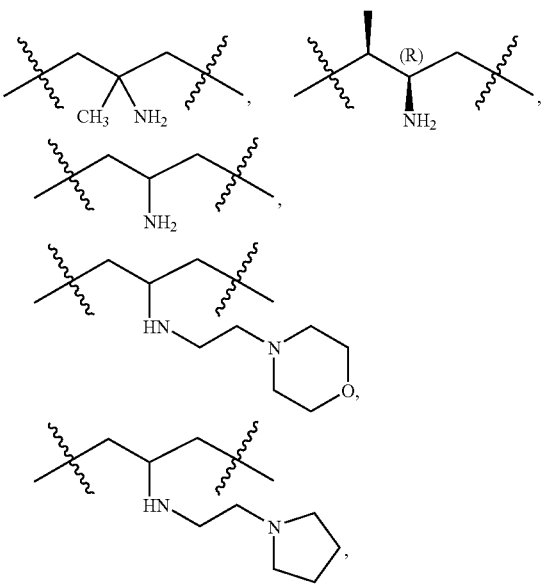

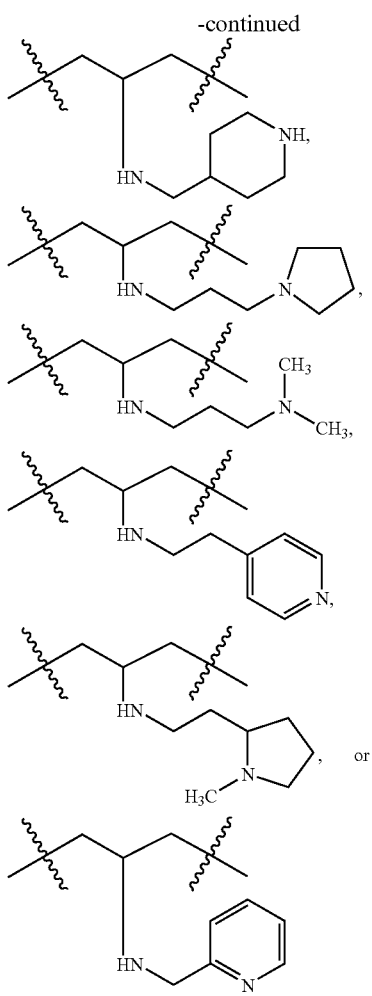

A specific group of compounds are compounds of formula (I) wherein X is a direct bond and $R_3$ is 3,5-dimethylpyrazol-1-yl, 2-phenylimidazol-1-yl, 2-ethylimidazol-1-yl, 1-benzimidazolyl, 4-(methoxycarbonyl)imidazol-1-yl, 4-methyl-2-ethylimidazol-1-yl, or 4-phenyl-1-imidazol-1-yl.

A specific group of compounds are compounds of formula (I) wherein X is oxygen and $R_3$ is 3,5-dichlorophenyl, 2-thien-2-ylethyl, 4-methylbenzyl, 4-methoxyphenethyl, 4-methylphenethyl, 3-(benzyloxy)propyl, 2-[3-(6-methylpyrid-2-yl)propyloxy]ethyl, 2-(ethoxy)ethyl, 3-(ethoxy)propyl, benzyl, cyclopropylmethyl, 4-(butoxy)benzyl, 2-(cyclohexyloxy)ethyl, pentyl, 3-phenylpropyl, 2-[(2-(ethoxy)ethoxy]ethyl, 2-phenylbenzyl, 3-(N,N-dimethyl)propyl, 3-(ethoxy)propyl, tert-butyl, 2-(phenoxy)ethyl, 2-pyrid-4-yl)ethyl, 2-methylphenyl, 2-chloro-6-methylphenyl, 2,4,6-trimethylphenyl, 2,6-dimethylphenyl, 2,4-dimethylphenyl, 3,4-methylenedioxy)benzyl, 3-(pyrid-3-yl)propyl, or 4-(N,N-dimethyl)phenethyl.

A specific group of compounds are compounds of formula (I) wherein $A_1$ is methylene or 1,1-ethanediyl, and $A_2$ is methylene.

A specific group of compounds are compounds of formula (I) wherein $R_8$ is $NR_{10}R_{11}$; and $R_{11}$ is heterocyclealkyl, heteroarylalkyl, or alkyl.

A specific group of compounds are compounds of formula (I) wherein $R_8$ is $NR_{10}R_{11}$; $R_{10}$ is hydrogen; and $R_{11}$ is 2-morpholinoethyl, 2-(pyrrolidin-1-yl)ethyl, 4-piperidinylmethyl, 3-N,N-dimethylamino)propyl, 2-(1-methyl-pyrrolidin-2-yl)ethyl, 2-(4-pyridyl)ethyl, or 3-(pyrrolidin-1-yl)propyl.

Specifically, $A_6$ can be methylene or 1,1-ethanediyl.
Specifically, $A_7$ can be methylene.
Specifically, each $R_{20}$ can independently be alkyl, substituted alkyl, alkoxy, substituted alkoxy, cyano, trifluoromethyl, halo, or $NR_4R_5$.
Specifically, $R_2$, can be hydrogen or methyl.
Specifically, each $R_{22}$ can independently be alkyl, substituted alkyl, alkoxy, substituted alkoxy, cyano, trifluoromethyl, halo, or $NR_4R_5$.

A specific group of compounds are compounds of formula (III) wherein $A_6$ is methylene or 11,1-ethanediyl and $A_7$ is methylene.

Specifically, $A_8$ can be methylene.
Specifically, $A_9$ can be methylene.
Specifically, each $R_{23}$ can independently be alkyl, substituted alkyl, alkoxy, substituted alkoxy, cyano, trifluoromethyl, halo, or $NR_4R_5$.
Specifically, $R_{24}$ can be hydrogen or methyl.
Specifically, $R_{25}$ is 2-morpholinoethyl, 2-(pyrrolidin-1-yl)ethyl, 4-piperidinylmethyl, 3-(N,N-dimethylamino)propyl, 2-(1-methyl-pyrrolidin-2-yl)ethyl, 2-(4-pyridyl)ethyl, 3-(pyrrolidin-1-yl)propyl, 2-[2-(ethoxy)ethoxy]ethyl, 3-(ethoxy)propyl, benzyl, cyclopropylmethyl, 2-(1-methylpyrrolidin-2-yl)ethyl, 2-(pyrid-4-yl)ethyl, pentyl, 3-phenylpropyl, 3,4-(methylenedioxy)benzyl, 3-(pyrid-3-yl)propyl, 4-(N,N-dimethyl)phenethyl, 4-(butoxy)benzyl, 2-(cyclohexyloxy)ethyl, 3,5-dichlorophenyl, 2-(thien-2-yl)ethyl, 4-methylbenzyl, 2-phenylbenzyl, 3-(N,N-dimethyl)propyl, tert-butyl, 2-(phenoxy)ethyl, 2-[3-(6-methylpyrid-2-yl)propyloxy]ethyl, 2-(ethoxy)ethyl, 4-methoxyphenethyl, 4-methylphenethyl, or 3-(benzyloxy)propyl.

A specific group of compounds are compounds of formula (IV) wherein $A_8$ is methylene and $A_9$ is methylene.

Specifically, $A_{10}$ can be methylene.
Specifically, $A_{11}$ can be methylene.
Specifically, each $R_{26}$ can independently be alkyl, substituted alkyl, alkoxy, substituted alkoxy, cyano, trifluoromethyl, halo, or $NR_4R_5$.
Specifically, $R_{27}$ can be hydrogen or methyl.
Specifically, $R_2$, can be 3,5-dimethylpyrazol-1-yl, 2-phenylimidazol-1-yl, 2-ethylimidazol-1-yl, 1-benzimidazolyl, 4-(methoxycarbonyl)imidazol-1-yl, 4-methyl-2-ethylimidazol-1-yl, or 4-phenylimidazol-1-yl.

A specific group of compounds are compounds of formula (V) wherein $A_{10}$ is methylene and $A_{11}$ is methylene.

Specifically, $A_{12}$ can be methylene or 1,1-ethanediyl.
Specifically, $A_{13}$ can be methylene.
Specifically, each $R_{29}$ can independently be alkyl, substituted alkyl, alkoxy, substituted alkoxy, cyano, trifluoromethyl, halo, or $NR_4R_5$.
Specifically, each $R_{30}$ can independently be alkyl, substituted alkyl, alkoxy, substituted alkoxy, cyano, trifluoromethyl, halo, or $NR_4R_5$.
Specifically, $R_3$, can be hydrogen or methyl.
Specifically, $R_{32}$ is 2-morpholinoethyl, 2-(pyrrolidin-1-yl)ethyl, 4-piperidinylmethyl, 3-(N,N-dimethylamino)propyl, 2-(1-methylpyrrolidin-2-yl)ethyl, 2-(4-pyridyl)ethyl, or 3-(pyrrolidin-1-yl)propyl.

A specific group of compounds are compounds of formula (VI) wherein $A_{12}$ is methylene or 1,1-ethanediyl, and $A_{13}$ is methylene.

General Synthetic Procedures

Generally, the compounds of the invention can be prepared using procedures that are known in the field of synthetic chemistry. Additionally, the Examples below describe the preparation of representative compounds of the invention. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, N.Y., 1999, and references cited therein.

Processes for preparing compounds of formulas I and III–VI are provided as further embodiments of the invention and are illustrated in the examples and schemes.

Pharmaceutical Compositions

The invention also provides pharmaceutical compositions comprising a compound of the invention. Accordingly, the compound, preferably in the form of a pharmaceutically acceptable salt, can be formulated for oral or parenteral administration for the therapeutic or prophylactic treatment of diseases or conditions associated with sodium channel activity.

By way of illustration, the compound can be admixed with conventional pharmaceutical carriers and excipients and used in the form of tablets, capsules, elixirs, suspensions, syrups, wafers, and the like. Such pharmaceutical compositions will contain from about 0.1 to about 90% by weight of the active compound, and more generally from about 10 to about 30%. The pharmaceutical compositions may contain common carriers and excipients, such as corn starch or gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat.

No. 5,023,252, issued Jun. 11, 1991. Such patches may be constructed for continuous, pulsatile, or on demand delivery of pharmaceutical agents.

The active compound is effective over a wide dosage range and is generally administered in a therapeutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses are in the general range of from 0.01–100 mg/kg/day, preferably 0.1–50 mg/kg/day. For an average 70 kg human, this would amount to 0.7 mg to 7 g per day, or preferably 7 mg to 3.5 g per day.

In general, an effective amount of a compound of this invention is a dose between about 0.5 and about 100 mg/kg. A preferred dose is from about 1 to about 60 mg/kg of active compound. A typical daily dose for an adult human is from about 50 mg to about 5 g.

According to the invention, a compound can be administered in a single daily dose or in multiple doses per day. The treatment regimen may require administration over extended periods of time, for example, for several days, for from one to six weeks, or longer.

Suitable formulations for use in the present invention can be found in *Remington's Pharmaceutical Sciences*, Mace Publishing Company, Philadelphia, Pa., 17th ed. (1985). The following non-limiting examples illustrate representative pharmaceutical compositions of the invention.

FORMULATION EXAMPLE A

This example illustrates the preparation of a representative pharmaceutical composition for oral administration of a compound of this invention:

| Ingredients | Quantity per tablet, (mg) |
| --- | --- |
| Active Compound | 200 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
| --- | --- |
| Active Compound | 400 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
| --- | --- |
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
| --- | --- |
| Active Compound | 0.2 g |
| Sodium Acetate Buffer Solution (0.4 M) | 2.0 mL |
| HCl (1 N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 g of the compound of this invention. Before use, the solution is then diluted with 200 mL of an intravenous fluid that is compatible with the active compound. Such fluids are chosen from 5% dextrose solution, 0.9% sodium chloride, or a mixture of 15% dextrose and 0.9% sodium chloride. Other examples are lactated Ringer's injection, lactated Ringer's plus 5% dextrose injection, Normosol-M and 5% dextrose, Isolyte E, and acylated Ringer's injection.

FORMULATION EXAMPLE F

This example illustrates the preparation of a representative pharmaceutical composition containing a compound of this invention.

An injectable preparation is prepared having the following composition:

| Ingredients | |
| --- | --- |
| Active Compound | 0.1–5.0 g |
| Hydroxypropyl-β-cyclodextrin | 1–25 g |
| 5% Aqueous Dextrose Solution (sterile) | q.s. to 100 mL |

The above ingredients are blended and the pH is adjusted to 3.5±0.5 using 0.5 N HCl or 0.5 N NaOH.

FORMULATION EXAMPLE G

This example illustrates the preparation of a representative pharmaceutical composition for topical application of a compound of this invention.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE H

This example illustrates the preparation of a representative pharmaceutical composition containing a compound of this invention.

A suppository totaling 2.5 grams is prepared having the following composition:

| Ingredients | |
| --- | --- |
| Active Compound | 500 mg |
| Witepsol H-15* | balance |

(*triglycerides of saturated vegetable fatty acid; a product of Riches-Nelson, Inc., New York, N.Y.)

Utility

The compounds of this invention, and their pharmaceutically acceptable salts, exhibit biological activity and are useful for medical treatment. The ability of a compound to block sodium channel activity or to treat neuropathic pain can be demonstrated using the tests described herein, or can be demonstrated using tests that are known in the art.

The following synthetic and biological examples are offered to illustrate the invention, and are not to be construed in any way as limiting the scope of the invention.

EXAMPLES

In the examples below, the following abbreviations have the following meanings. Any abbreviations not defined have their generally accepted meaning. Unless otherwise stated, all temperatures are in degrees Celsius.

| BOC, Boc = | tert-butoxycarbonyl |
| --- | --- |
| DMSO = | dimethyl sulfoxide |
| TFA = | trifluoroacetic acid |
| THF = | tetrahydrofuran |
| MgSO$_4$ = | anhydrous magnesium sulfate |

General: Starting material (including alcohols, phenols, di-ols, amines, and etc.) and solvents were purchased from commercial suppliers (Aldrich, Fluka, Sigma, and etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly it was purified by flash column chromatography with silica gel. Other purification methods include temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR, samples were dissolved in deuterated solvent (CD$_3$OD, CDCl$_3$, or DMSO-d$_6$), and $^1$H-NMR spectra were acquired with a Varian Gemini 2000 instrument (300 MHZ) under standard observe parameters. Mass spectrometric identification of compounds was performed by an electrospray ionization method (ESMS) with a Perkin Elmer instrument (PE SCIEX API 150 EX).

Analytical HPLC: Each crude compound was dissolved in 50% MeCN/H$_2$O (with 0.1% TFA) at 0.5–1.0 mg/mL concentration, and was analyzed by using anal. HPLC: 1) reverse-phased anal. column, Bonus-RP (2.1×50 mm; ID=5 mm); 2) flow rate: 0.5 mL/min; 3) 10% MeCN/H$_2$O (0.1% TFA) (0–0.5 min), 10 to 70% (linear gradient; 0.5–5 min); 4) detection: 214, 254, and 280 nm. Other conditions used are indicated whenever necessary.

A general protocol for preparative HPLC purification: Crude compounds were dissolved in 50% MeCN/H$_2$O (with 0.1% TFA) at 3045 mg/mL concentration, filtered, and injected into a reversed column. The following represents a typical method selected from various purification conditions:

1) column; YMC Pack-Pro C18 (50a×20 mm; ID=5 mm); 2) linear gradient: 10 to 60% MeCN (0.1% TFA)/H$_2$O (0.1% TFA) over 30 min; 3) flow rate: 40 mL/min; 4) detection: 214, 254, or 280 nm.

The preparation of compound (1) is illustrated in Scheme 1.

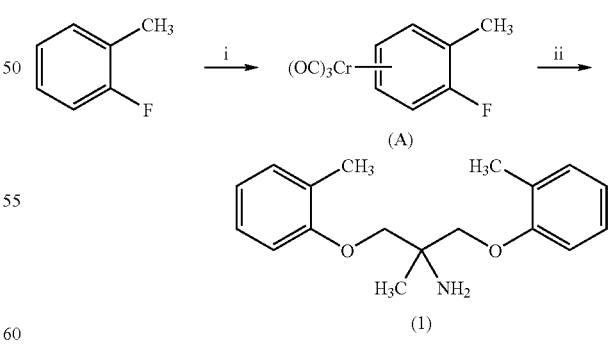

Example 1

Preparation of Compound (1)

To a cold suspension of NaH (60% oily dispersion; 0.943 g, ~24 mmol) in anhydrous THF (200 mL) in ice bath was added 2-amino-2-methyl-1,3-propanediol (0.991 g, 9.4 mmol) under stream of nitrogen gas. The mixture was stirred for 30 min at the same temperature prior to addition of 2-fluorotoluene-chromium tricarbonyl complex ((A); 5.8 g, 23.6 mmol). The final mixture was stirred in ice bath for 3 h, and at rt for 48 h. The reaction mixture was quenched by cooling in ice bath, and followed by slow addition of iodine (23 g, 90.6 mmol) over 5 min while stirring the mixture. After the addition, the mixture was stirred for 1 h in ice bath, and treated carefully with water (10 mL) under nitrogen gas. It was then concentrated in vacuo, to afford dark brown residue, and partitioned between EtOAc (400 mL) and brine solution (200 mL). The organic phase was collected, and washed with 5% $Na_2S_2O_3$ (200 mL). After drying over $MgSO_4$, the organic solution was concentrated in vacuo, yielding pale yellow oil. It was dissolved in ~16 mL of aqueous acetonitrile (60%) containing 5% TFA, filtered through a membrane filter, and purified by preparative reverse-phase HPLC as described above. The desired product (Compound (1)) was obtained after HPLC purification as TFA salt as thick oil (2.3 g; 61%). It was solidified slowly to pale yellow solid. Retention time (anal. HPLC: 10–70% $MeCN/H_2O$ over 5 min)=3.6 min. ESMS ($C_{18}H_{23}NO_2$): calcd. 285.4; obsd. 286.1 $[M+H]+^+$.

Compound (A): (See FIG. 1) was synthesized according to literature procedures (F. Rose-Munch, E. Rose, A. Semra, L. Mignon, J. Garcia-Oricain, E. C. Knobler, *J. Organometallic Chem.* 1989, 363, 297–309). To a round-bottomed flask (250 mL) equipped with a reflux condenser was added $nBu_2O$ (100 mL), tetrahydrofuran (30 mL), 2-fluorotoluene (12.3 g, 112 mmol), and chromium hexacarbonyl (10 g, 45.4 mmol). The suspension was saturated with nitrogen gas, and then stirred under nitrogen atmosphere while increasing the temperature of the reaction mixture gradually to 125° C. over 20 min. It was refluxed at the same temperature for 24 h, and cooled to rt. To the mixture was added second portion of tetrahydrofuran (20 mL). The final mixture was refluxed for another 24 h at 125° C. After cooling of the mixture to rt, white crystalline solid was precipitated. It was separated from the pale green-yellow solution by filtration through a filter paper on Buchner funnel, and rinsed with $nBu_2O$ (100 mL). The filtrates were combined, and concentrated to dryness, yielding yellow solid as a desired product (2.3 g). It was kept in a brown bottle, and used in next step without further purification. $^1$H-NMR ($CD_3OD$, 299.96 MHZ): d (ppm) 5.64 (br s, 1H), 5.51 (brs, 1H), 5.1 (brs, 1H), 4.86 (br s, 1H), 2.21 (br s, 3H).

The preparation of compounds (2)–(4) is illustrated in Scheme 2.

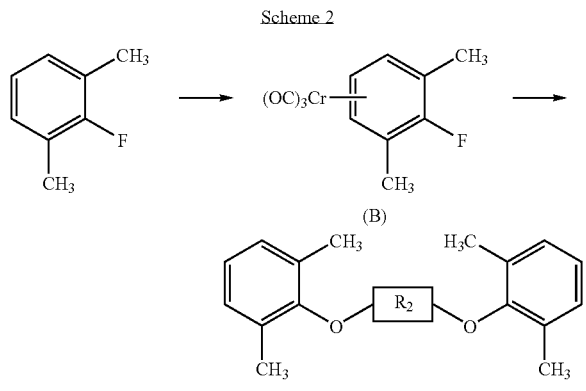

Scheme 2

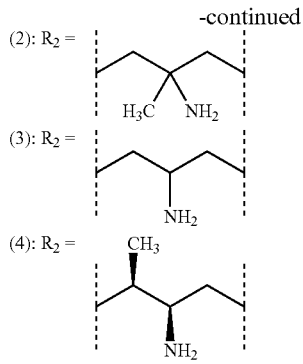

Example 2

Preparation of Compound (2)

To a cold suspension of NaH (60% oily dispersion; 83 mg, 2.1 mmol) in anhydrous THF (15 mL) in ice bath was added 2-amino-2-methyl-1,3-propanediol (87 mg, 0.83 mmol) under stream of nitrogen gas. The mixture was stirred for 1 h at the same temperature prior to addition of 2-fluoro-m-xylene-chromium tricarbonyl complex ((B); 538 mg, 2.1 mmol). The final mixture was stirred in ice bath for 1 h, and at rt for 48 h. The reaction mixture was quenched by cooling in ice bath, and followed by slow addition of iodine (2.0 g, 7.9 mmol) over 5 min while stirring the mixture. After the addition, the mixture was stirred for 1 h in ice bath, and treated carefully with water (1 mL) under nitrogen gas. It was then concentrated in vacuo, to afford dark brown residue, and partitioned between EtOAc (150 mL) and brine solution (100 mL). The organic phase was collected, and washed with 5% $Na_2S_2O_3$ (50 mL). After drying over $MgSO_4$, the organic solution was concentrated in vacuo, yielding pale yellow oil. It was dissolved in ~5 mL of aqueous acetonitrile (60%) containing 5% TFA, filtered through a membrane filter, and purified by preparative reverse-phase HPLC as described previously. The desired product (Compound (2)) was obtained as TFA salt (71 mg). Retention time (anal. HPLC: 10 to 70% $MeCN/H_2O$ over 5 min)=3.84 min. ESMS ($C_{20}H_{27}NO_2$): calcd. 313.4; obsd. 314.3 $[M+H]^+$.

Compound (B) was prepared similarly as described for compound (A) by using $nBu_2O$ (100 mL), tetrahydrofuran (30 mL), 2-fluoro-m-xylene (12 g, 97 mmol), and chromium hexacarbonyl (10 g, 45.4 mmol). The product was obtained as yellow solid (3.3 g). It was kept in a brown bottle, and used in next step without further purification. $^1$H-NMR ($CD_3OD$, 299.96 MHZ): d (ppm) 5.45 (br s, 1H), 5.2 (br s, 1H), 4.88 (br s, 1H), 2.24 (br s, 6H).

Example 3

Preparation of Compound (3)

Compound 3 was synthesized in a similar manner to compound (2) using arene-chromium complex (B) and 2-amino-1,3-propanediol. Retention time (anal. HPLC: 10–70% $MeCN/H_2O$ over 5 min)=3.75 min. ESMS ($C_{19}H_{25}NO_2$): calcd. 299.4; obsd. 300.2 $[M+H]^+$.

Example 4

Preparation of Compound (4)

Compound (4) was synthesized in a similar manner to compound (2) using arene-chromium complex (B) and (L)-threoninol. Retention time (anal. HPLC: 10–70% MeCN/H$_2$O over 5 min)=3.85 min. ESMS (C$_{20}$H$_{27}$NO$_2$): calcd. 313.4; obsd. 314.3 [M+H]$^+$.

The preparation of compounds (5)–(6) is illustrated in Scheme 3.

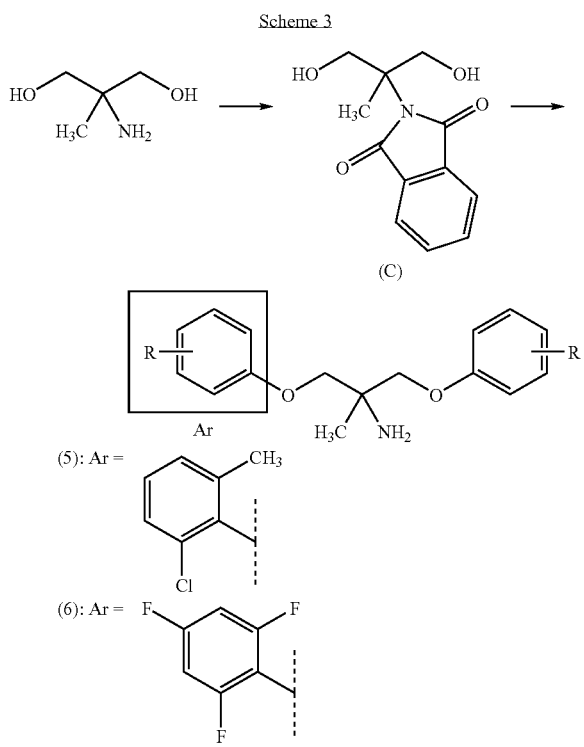

Example 5

Preparation of Compound (5)

To a cold solution of compound (C) (1.5 g, 6.37 mmol), 2-chloro-6-methylphenol (2.18 g, 15.3 mmol), and triphenylphosphine (4.0 g, 15.3 mmol) in anhydrous THF (50 mL) in ice bath was added diethyl azadicarboxylate (2.44 g, 14 mmol) under nitrogen atmosphere. The mixture was stirred for 4 h in ice bath, and for 48 h at rt. After concentration of the mixture in vacuo, an oily residue was obtained. It was dissolved in EtOAc (200 mL), and washed with 5% NaOH and then with brine solution. The crude product was dissolved in EtOH (50 mL), and followed by addition of hydrazine monohydrate (7 mL). The final mixture was heated at 90° C. for 12 h. After cooling to rt, the mixture was filtered through a filter paper to remove white precipitate. The filtrate was concentrated in vacuo, yielding oily residue. It was dissolved in 60% aqueous acetonitrile (5% TFA), and purified by preparative reverse-phase HPLC (20 to 70% MeCN/water over 30 min; 254 run). Retention time (anal. HPLC: 10–70% MeCN/H$_2$O over 5 min)=3.8 min. ESMS (C$_{18}$H$_{21}$Cl$_2$NO$_2$): calcd. 354.3; obsd. 353.9 [M]$^+$.

Compound (C) was prepared as follows. A mixture of 2-amino-2-methyl-1,3-propanediol (5 g, 47.6 mmol) and N-carboethoxyphthalimide (10.95 g, 50 mmol) in chloroform (100 mL) was heated at 75° C. for 24 h. The mixture was concentrated in vacuo, yielding colorless oily residue. It was partitioned between EtOAC (200 mL) and brine solution (200 mL). After shaking, the organic phase was dried over MgSO$_4$, and concentrated to oily residue. The crude product was purified by flash silica column chromatography by eluting with 50% EtOAc/hexane to 1% MeOH in 70% EtOAc/hexane. Compound (C) was obtained as white solid (9.8 g; 88%). R$_f$=0.5 (5% MeOH in 70% EtOAc/hexane). Retention time (anal. HPLC: 10–70% MeCN/H$_2$O over 5 min)=1.9 min. ESMS (C$_{12}$H$_{13}$NO$_4$): calcd. 235.2; obsd. 236.6 [M+H]$^+$, 471.7 [2M+H]$^+$. $^1$H-NMR (CD$_3$OD, 299.96 MHZ): d (ppm) 7.79–7.76 (m, 4H), 4.24.16 (d, 2H), 3.89–3.85 (d, 2H), 1.63 (s, 3H).

Example 6

Preparation of Compound (6)

Compound (6) was synthesized in a similar manner to compound (5) using 2,4,6-trifluorophenol. Retention time (anal. HPLC: 10–70% MeCN/H$_2$O over 5 min)=3.3 min. ESMS (C$_{16}$H$_{13}$F$_6$NO$_2$): calcd. 365.3; obsd. 365.9 [M+H]$^+$, 731.3 [2M+H]$^+$.

The preparation of compounds (7)–(9) is illustrated in Scheme 4.

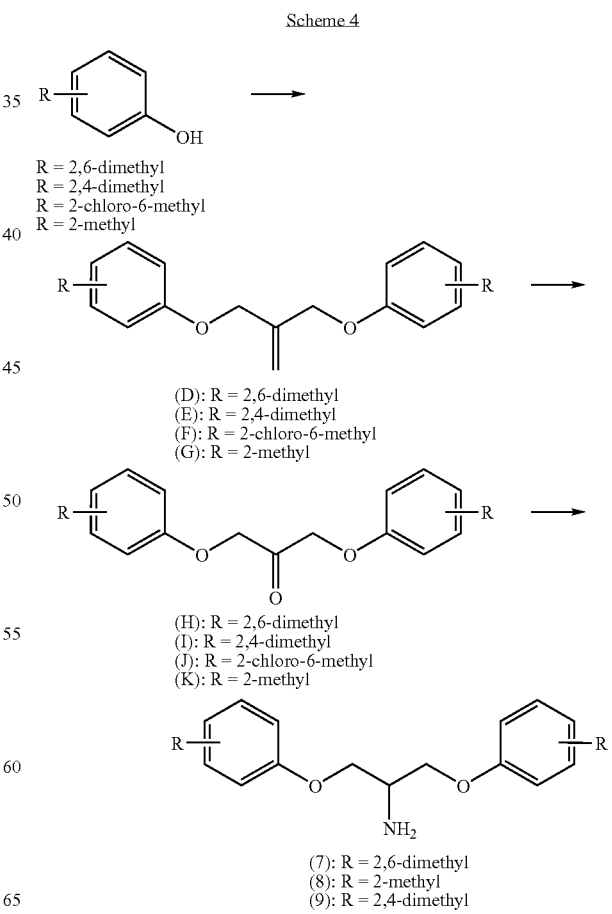

Example 7

Preparation of Compound (9)

A mixture of compound (1) (500 mg, 1.68 mmol), aq. NH$_3$ (conc; 5 mL), and NH$_4$OAc (1.0 g, 13 mmol) in ethanol (50 mL) was heated at 70° C. for 1 h, and cooled to OC prior to addition of sodium cyanoborohydride (158 mg, 2.5 mmol) in ice bath. After stirring for 1 h, the mixture was concentrated in vacuo, and the residue was dissolved in 50% aqueous acetonitrile (5% TFA). It was purified by preparative reverse-phase HPLC. Retention time (anal. HPLC: 10–70% MeCN/H$_2$O over 5 min)=4.0 min. ESMS (C$_{19}$H$_{21}$NO$_2$): calcd. 299.4; obsd. 300.2 [M+H]$^+$, 599.5 [2M+H]$^+$.

The intermediate compound (1) was prepared as follows.

a. Preparation of compound (E). Using a procedure similar to that described in Example 9, subpart a, except replacing the 2,6-dimethylphenol used therein with 2,4-dimethylphenol, compound (E) was prepared. R$_f$=0.91 in hexane/EtOAc (4/1).

$^1$H-NMR (CD$_3$OD, 299.96 MHZ): d (ppm) 6.92–6.88 (m, 4H), 6.77–6.74 (d, 2H), 5.35 (s, 2H), 4.61 (m, 4H), 2.21–2.14 (two s, 12H).

b. Preparation of compound (I). Using a procedure similar to that described in Example 9, sub-part b, except replacing the Compound (D) used therein with Compound (E), Compound (1) was prepared. $^1$H-NMR (CD$_3$OD, 299.96 MHZ): d (ppm) 6.9–6.6 (m, 6H), 4.84 (s, 4H), 2.19–2.07 (two s, 12H).

Example 8

Preparation of Compound (8)

Compound (8) was synthesized in a similar fashion to compound (7) using compound (K). Retention time (anal. HPLC: 10–70% MeCN/H$_2$O over 5 min)=3.58 min. ESMS (C$_{17}$H$_{21}$NO$_2$): calcd. 271.4; obsd. 272.0 [M+H]$^+$. $^1$H-NMR (CD$_3$OD, 299.96 MHZ): d (ppm) 7.2–7.13 (m, 4H), 7.0–6.88 (m, 4H), 4.39–4.36 (m, 4H), 4.15–4.1 (quin, 1H).

The intermediate compound (K) was prepared as follows.

a. Using a procedure similar to that described in Example 9, sub-part a, except replacing the 2,6-dimethylphenol used therein with 2-methylphenol, compound (G) was prepared. R=0.91 in hexane/EtOAc (4/1). $^1$H-NMR (CD$_3$OD, 299.96 MHZ): d (ppm) 7.11–7.08 (m, 4H), 7.09–6.81 (m, 4H), 5.39–5.38 (m, 2H), 4.68–4.65 (m, 4H), 2.18 (s, 6H).

b. Preparation of compound (K). Using a procedure similar to that described in Example 9, sub-part b, except replacing the Compound (D) used therein with Compound (G), Compound (K) was prepared. $^1$H-NMR (CD$_3$OD, 299.96 MHZ): d (ppm) 7.18–7.06 (m, 4H), 6.95–6.80 (m, 4H), 4.87 (s, 4H), 2.1 (s, 6H).

Example 9

Preparation of Compound (7)

Using a procedure similar to that described in Example 7, except replacing the Compound (I) used therein with Compound (H), the title compound was prepared. Retention time (anal. HPLC: 10–70% MeCN/H$_2$O over 5 min)=3.7 min. ESMS (C$_{19}$H$_{25}$NO$_2$): calcd. 299.4; obsd. 300.2 [M+H]$^+$, 599.2 [2M+H]$^+$.

The intermediate compound (H) was prepared as follows.

a. Preparation of compound (D). To a nitrogen-saturated solution of 2,6-dimethylphenol (17.2 g, 0.14 mole) and 3-chloro-2-chloromethyl-1-propene (8.0 g, 0.064 mole) in acetone (250 mL) was added K$_2$CO$_3$ (19.46 g, 0.141 mole). The mixture was stirred and refluxed under nitrogen for 72 h. The mixture was cooled to rt, and filtered through a filter paper on Buchner funnel. The filtrate was concentrated in vacuo, yielding colorless oily residue. It was purified by silica column chromatography by eluting with hexane/EtOAc (8/1). The desired product (compound (D)) was obtained as colorless oil (16.5 g; 87%). R$_f$=0.77 in hexane/EtOAc (8/1). $^1$H-NMR (CD$_3$OD, 299.96 MHZ): d (ppm) 7.0–6.98 (d, 4H), 6.81–6.7 (dd, 2H), 5.46 (s, 2H), 4.44 (s, 4H), 2.26 (s, 12H).

b. Preparation of Compound (H). To a cold solution of compound (D) (15.5 g, 52.3 mmol) in dioxane (350 mL) was added water (60 mL) and NaIO$_4$ (24 g, 110 mmol) in ice bath. After stirring the mixture for 10 min, OsO4 (1 g) in tBuOH (25 mL) was added to it. The final mixture was stirred for 4 h in ice bath, and 20 h at rt. The mixture was filtered through a filter paper, and the solid residue was rinsed with EtOAc (300 mL). The filtrate was washed with brine solution (200 mL), dried over MgSO$_4$, and concentrated in vacuo, yielding pale brown oil. It was purified by silica column chromatography by eluting with hexane/EtOAc (9/1 to 3/1). Fractions with R$_f$ of 0.71 (25% EtOAc/hexane) were collected, and concentrated to afford pale brown solid. It was crystallized using small amount of hexane at 0° C. Compound (H) was obtained as white solid in 40% yield (6.24 g). Retention time (anal. HPLC: 10–70% MeCN/H$_2$O over 5 min)=4.9 min. $^1$H-NMR (CD$_3$OD, 299.96 MHZ): d (ppm) 7.1–7.0 (d, 4H), 6.9–6.8 (dd, 2H), 4.75 (s, 4H), 2.27 (s, 12H).

The preparation of compounds (10)–(17) is illustrated in Scheme 5.

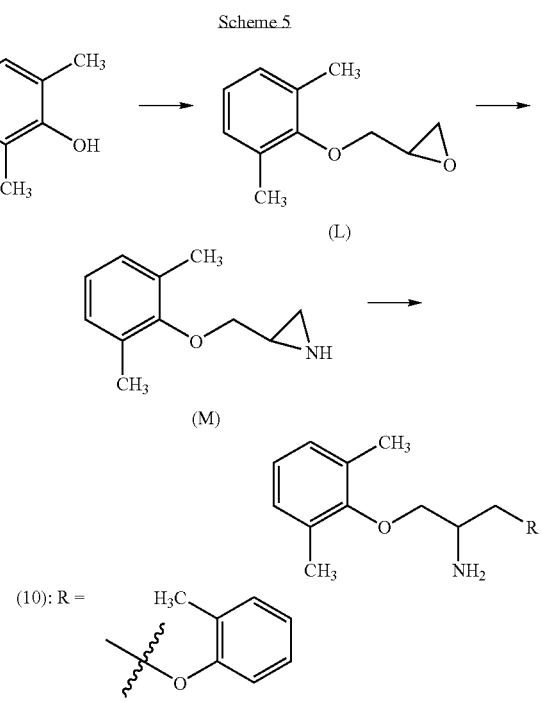

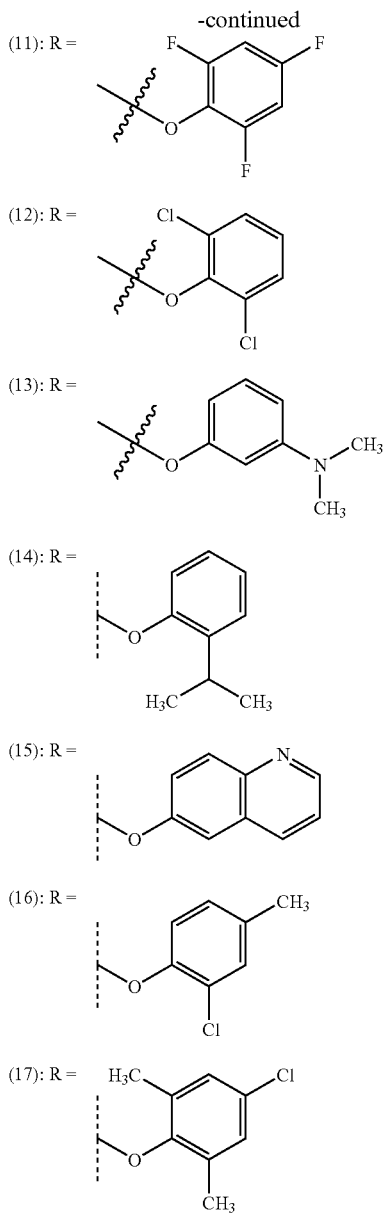

Example 10

Preparation of Compound (10)

A mixture of compound (M) (0.5 g, 2.82 mmol), o-cresol (0.61 g, 5.6 mmol), and $BF_3Et_2O$ (1 mL, 7.9 mmol) in toluene (10 mL) was heated at 90° C. for 24 h. After cooling to rt, the mixture was treated with 5% TFA/50% aqueous acetonitrile (10 mL), and followed by concentration in vacuo. The resulting residue was dissolved in aqueous acetonitrile, and purified by preparative reverse HPLC. The desired product, compound (10), was obtained as TFA salt (180 mg). Retention time (anal. HPLC: 10–70% MeCN/$H_2O$ over 5 min)=3.6 min. ESMS ($C_{18}H_{23}NO_2$): calcd. 285.4; obsd. 286.1 [M+H]$^+$, 571.3 [2M+H]$^+$. $^1$H-NMR ($CD_3OD$, 299.96 MHZ): d (ppm) 7.2–7.15 (m, 2H), 7.02–6.88 (m, 5H), 4.45–4.35 (m, 2H), 4.24.18 (m, 2H), 4.11–4.05 (quin; 1H), 2.28 (m, 9H).

The intermediate compound (M) was prepared as follows.

a. Preparation of compound (L). To a nitrogen-saturated, cold suspension of 2,6-dimethylphenol (20 g, 0.164 mole) in water (200 mL) in ice bath was added NaOH (7.86 g, 0.197 mole), and then followed by addition of 2-chloromethyloxirane (27.3 g, 0.295 mole). After stirring the mixture in ice bath for 1 h, it was stirred for 24 h at rt under nitrogen atmosphere. The mixture was then extracted with 40% EtOAc/hexane (300 mL). The organic layer was washed with 1M NaOH (2×150 mL), dried over $MgSO_4$, and concentrated in vacuo, yielding pale yellow oil. It was purified by silica column chromatography by eluting with hexane/EtOAc (8/1 to 5/1). Compound (L) was obtained as colorless liquid (14.87 g, 51%). $R_f$=0.73 in hexane/EtOAc (3/1). $^1$H-NMR ($CD_3OD$, 299.96 MHZ): d (ppm) 7.0–6.96 (d, 2H), 6.9–6.85 (dd, 1H), 4.12–4.08 (dd, 1H), 3.68–3.6 (dd, 1H), 3.35–3.3 (m, 1H), 2.88–2.82 (t, 1H), 2.7–2.65 (m, 1H), 2.25 (s, 6H).

b. Preparation of compound (M). To a cold solution of compound (L) (14.87 g, 83.4 mmol) in 2-ethoxyethanol (125 mL) and water (40 mL) in ice bath was added sodium azide (10.86 g, 166.8 mmol) and ammonium sulfate (13.23 g, 100.1 mmol). After stirring the mixture for 2 h in ice bath, it was stirred at rt for 36 h. The mixture was extracted with ether (2×300 mL). The organic layer was washed with brine solution, dried over $MgSO_4$, and evaporated to dryness, yielding colorless oil (17.6 g). $^1$H-NMR ($CD_3OD$, 299.96 MHZ): d (ppm) 7.0–6.96 (d, 2H), 6.95–6.92 (t, 1H), 4.1–4.08 (m, 1H), 3.79–3.74 (m, 2H), 3.57–3.4 (m, 2H), 2.26 (s, 6H).

The above product was dissolved in acetonitrile (50 mL), and then added slowly to a solution of triphenylphosphine (21.9 g, 83.5 mmol) in acetonitrile (400 mL) while being stirred. The mixture was stirred for 3 h at rt under stream of nitrogen, and then heated at 90° C. for 6 h. The mixture was cooled, concentrated in vacuo, yielding white semicrystalline oil. It was purified by silica column chromatography by eluting with 50% EtOAc/hexane to 5% MEOH in 50% EtOAc/hexane. Compound (M) was obtained as colorless oil (8 g, 54%). Retention time (anal. HPLC: 10–70'/% MeCN/$H_2O$ over 5 min)=1.8 min. ESMS ($C_{11}H_{15}NO$): calcd. 177.2; obsd. 201.1 [M+Na]$^+$. $^1$H-NMR ($CD_3OD$, 299.96 MHZ): d (ppm) 7.0–6.97 (d, 2H), 6.95–6.90 (t, 1H), 3.82–3.81 (dd, 1H), 3.72–3.65 (dd, 1H), 2.45–2.4 (m, 1H), 2.27 (s, 6H), 1.9 (d, 1H), 1.75 (m, 1H).

Example 11

Preparation of Compound (11)

Compound (11) was synthesized in a similar manner to that described in Example 10, except replacing the 2,6-dimethylphenol used in sub-part a, with 2,4,6-trifluorophenol. Retention time (anal. HPLC: 10–70% MeCN/$H_2O$ over 5 min)=3.5 min. ESMS ($C_{17}H_{18}F_3NO_2$): calcd. 325.3; obsd. 326.0 [M+H]$^+$, 348.2 [M+Na]$^+$.

Example 12

Preparation of Compound (12)

Compound (12) was synthesized in a similar manner to that described in Example 10, except replacing the 2,6- dimethylphenol used in sub-part a with 2,6-dichlorophenol. Retention time (anal. HPLC: 10–70% MeCN/H$_2$O over 5 min)=3.71 min. ESMS (C$_{17}$H$_{19}$Cl$_2$NO$_2$): calcd. 340.2; obsd. 340.1 [M]$^+$.

Example 13

Preparation of Compound (13)

Compound (13) was synthesized in a similar manner to that described in Example 10, except replacing the 2,6-dimethylphenol used in sub-part a with 3-N,N-dimethylaminophenol. Retention time (anal. HPLC: 5–75% MeCN/H$_2$O over 4 min)=2.1 min. ESMS (C$_{19}$H$_{26}$N$_2$O$_2$): calcd. 314.4; obsd. 315.2 [M+H]$^+$.

Example 14

Preparation of Compound (14)

Compound (14) was synthesized in a similar manner to that described in Example 10, except replacing the 2,6-dimethylphenol used in subpart a with 2-isopropylphenol. Retention time (anal. HPLC: 5–75% MeCN/H$_2$O over 4 min)=3.3 min. ESMS (C$_2$H$_{27}$NO$_2$): calcd. 313.4; obsd. 314.0 [M+H]$^+$.

Example 15

Preparation of Compound (15)

Compound (15) was synthesized in a similar manner to that described in Example 10, except replacing the 2,6-dimethylphenol used in sub-part a with 6-hydroxyquinoline. Retention time (anal. HPLC: 5–75% MeCN/H$_2$O over 4 min)=2.2 min. ESMS (C$_{20}$H$_{22}$N$_2$O$_2$): calcd. 322.4; obsd. 323.0 [M+H]$^+$.

Example 16

Preparation of Compound (16)

Compound (16) was synthesized in a similar manner to that described in Example 10, except replacing the 2,6-dimethylphenol used in sub-part a with 2-chloro-4-methylphenol. Retention time (anal. HPLC: 5–75% MeCN/H$_2$O over 4 min)=3.4 min. ESMS (C$_{18}$H$_{22}$ClNO$_2$): calcd. 319.8; obsd. 319.9 [M]$^+$.

Example 17

Preparation of Compound (17)

Compound (17) was synthesized in a similar manner to that described in Example 10, except replacing the 2,6-dimethylphenol used in sub-part a with 4-chloro-2,6-dimethylphenol. Retention time (anal. HPLC: 5–75% MeCN/H$_2$O over 4 min)=3.4 min. ESMS (C$_{19}$H$_{24}$ClNO$_2$): calcd. 333.8; obsd. 334.2 [M+H]$^+$.

The preparation of compounds (18)–(29) is illustrated in Scheme 6.

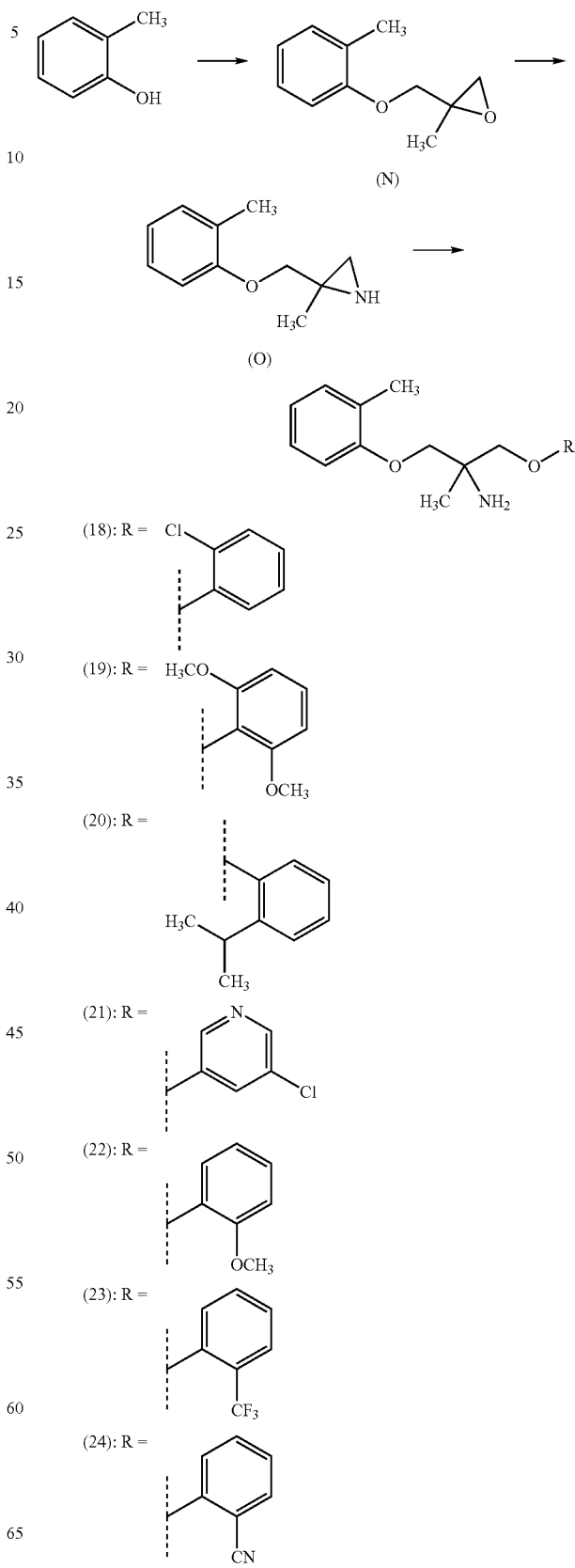

Scheme 6

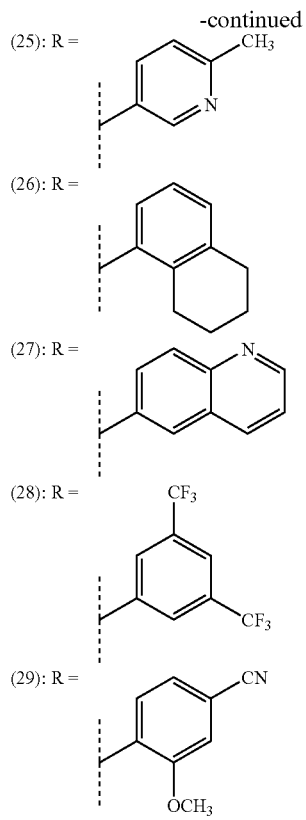

-continued (25): R = [pyridine with CH3]

(26): R = [tetrahydronaphthalene]

(27): R = [quinoline]

(28): R = [phenyl with two CF3]

(29): R = [phenyl with CN and OCH3]

Example 18

Preparation of Compound (18)

A mixture of compound (O) (35.5 mg, 0.2 mmol), 2-chlorophenol (25.6 mg, 0.2 mmol), and $BF_3Et_2O$ (28.4 mg, 0.2 mmol) in toluene (0.5 mL) was heated at 90° C. for 24 h. After cooling to rt, the mixture was treated with 5% TFA/50% aqueous acetonitrile (1 mL), and followed by concentration in vacuo. The resulting residue was dissolved in aqueous acetonitrile, and purified by preparative reverse HPLC. The desired product (compound (18)) was obtained as TFA salt. Retention time (anal. HPLC: 5–75% MeCN/$H_2O$ over 4 min)=3.0 min. ESMS ($C_{17}H_{20}ClNO_2$): calcd. 305.8; obsd. 306.1 [M+H]$^+$.

The intermediate compound (O) was prepared as follows.

a. Preparation of compound (N). To a nitrogen-saturated, cold suspension of o-cresol (11.28 g, 0.104 mole) in water (200 mL) in ice bath was added NaOH (5.01 g, 0.125 mole), followed by addition of 2-chloromethyl-2-methyloxirane (20.0 g, 0.188 mole). After stirring the mixture in ice bath for 1 h, it was stirred for 24 h at room temperature under nitrogen atmosphere. The mixture was then extracted with 40% EtOAc/hexane (300 mL). The organic layer was washed with 1M NaOH (2×150 mL), dried over MgSO$_4$, and concentrated in vacuo, yielding pale yellow oil. It was purified by silica column chromatography, eluting with hexane/EtOAc (8/1 to 5/1). Compound (N) was obtained as colorless liquid (11.3 g). R$_f$=0.57 in hexanel/EtOAc (5/1). Retention time (anal. HPLC: 10–70% MeCN/$H_2O$ over 5 min)=4.31 min. $^1$H-NMR (CD$_3$OD, 299.96 MHZ): δ (ppm) 7.13–7.08 (m, 2H), 6.86–6.78 (m, 2H), 4.12–4.09 (d, 1H), 3.89–3.86 (d, 1H), 2.89–2.87 (d, 1H), 2.74–2.72 (d, 1H), 2.21 (s, 3H), 1.46 (s, 3H).

b. Preparation of compound (O). To a cold solution of compound (N) (11.3 g, 0.063 mol) in 2-ethoxyethanol (130 mL) and water (30 mL) in ice bath was added sodium azide (8.26 g, 0.127 mol) and ammonium sulfate (10.06 g, 0.076 mol). After stirring the mixture for 2 h in ice bath, it was stirred at rt for 36 h. The mixture was extracted with ether (2×300 mL). The organic layer was washed with brine solution, dried over MgSO$_4$, and evaporated to dryness, yielding colorless oil (11.13 g). $^1$H-NMR (CD$_3$OD, 299.96 MHz): δ (ppm) 7.15–7.09 (m, 2H), 6.87–6.80 (m, 2H), 3.92–3.89 (d, 1H), 3.79–3.76 (d, 1H), 3.43–3.42 (m, 2H), 2.21 (s, 3H), 1.33 (s, 3H). Retention time (anal. HPLC: 10–70% MeCN/$H_2O$ over 5 min)=4.5 min. The above product was dissolved in acetonitrile (100 mL), and then added slowly to a solution of triphenylphosphine (13.85 g, 0.053 mol) in acetonitrile (100 mL) while being stirred. The mixture was stirred for 3 hours at room temperature under stream of nitrogen, and then heated at 90° C. for 6 h. The mixture was cooled, add concentrated in vacuo, yielding white semi-crystalline oil. It was purified by silica column chromatography by eluting with 50% EtOAc/hexane to 5% MeOH in 50% EtOAc/hexane. Compound (O) was obtained as colorless oil (4.7 g). Retention time (anal. HPLC: 10–70% MeCN/$H_2O$ over 5 min)=1.85 min. $^1$H-NMR (CD$_3$OD, 299.96 MHz): δ (ppm) 7.13–7.10 (m, 2H), 6.84–6.78 (m, 2H), 3.97–3.94 (d, 1H), 3.81–3.78 (d, 1H), 2.21 (s, 3H), 1.83 (s, 1H), 1.68 (s, 1H), 1.40 (s, 3H). ESMS ($C_{11}H_{15}NO$): calcd. 177.2; obsd. 223 [M+Na]$^+$.

Example 19

Preparation of Compound (19)

Compound (19) was synthesized in a similar manner to compound (18) using 2,6-dimethoxyphenol. Retention time (anal. HPLC: 5–75% MeCN/$H_2O$ over 4 min)=2.9 min. ESMS ($C_{19}H_{25}NO_4$): calcd. 331.4; obsd. 332.1 [M+H]$^+$.

Example 20

Preparation of Compound (20)

Compound (20) was synthesized in a similar manner to compound (18) using 2-isopropylphenol. Retention time (anal. HPLC: 5–75% MeCN/$H_2O$ over 4 min)=3.3 min. ESMS ($C_{20}H_{27}NO_2$): calcd. 313.4; obsd. 314.2 [M+H]$^+$.

Example 21

Preparation of Compound (21)

Compound (21) was synthesized in a similar manner to compound (18) using 3-chloro-5-hydroxypyridine and DMF as a solvent. Retention time (anal. HPLC: 5–75% MeCN/$H_2O$ over 4 min)=2.5 min. ESMS ($C_{16}H_{19}ClN_2O_2$): calcd. 306.8; obsd. 307.0 [M+H]$^+$.

Example 22

Preparation of Compound (22)

Compound (22) was synthesized in a similar manner to compound (18) using 2-methoxyphenol. Retention time (anal. HPLC: 5–75% MeCN/H$_2$O over 4 min)=2.9 min. ESMS (C$_{18}$H$_{23}$NO$_3$): calcd. 301.4; obsd. 302.1 [M+H]$^+$.

Example 23

Preparation of Compound (23)

Compound (23) was synthesized in a similar manner to compound (18) using 2-trifluoromethylphenol. Retention time (anal. HPLC: 5–75% MeCN/H$_2$O over 4 min)=3.1 min. ESMS (C$_{18}$H$_{20}$F$_3$NO$_2$): calcd. 339.4; obsd. 340.1 [M+H]$^+$.

Example 24

Preparation of Compound (24)

Compound (24) was synthesized in a similar manner to compound (18) using 2-cyanophenol. Retention time (anal. HPLC: 5–75% MeCN/H$_2$O over 4 min)=2.9 min. ESMS (C$_{18}$H$_{20}$N$_2$O$_2$): calcd. 296.4; obsd. 297.1 [M+H]$^+$.

Example 25

Preparation of Compound (25)

Compound (25) was synthesized in a similar manner to compound (18) using 6-methyl-3-hydroxypyridine and DMF as a solvent. Retention time (anal. HPLC: 5–75% MeCN/H$_2$O over 4 min)=1.6 min. ESMS (C$_{17}$H$_{22}$N$_2$O$_2$): calcd. 286.4; obsd. 287.1 [M+H]$^+$.

Example 26

Preparation of Compound (26)

Compound (26) was synthesized in a similar manner to compound (18) using 1-hydroxy-5,6,7,8-tetrahydronaphthalene. Retention time (anal. HPLC: 5–75% MeCN/H$_2$O over 4 min)=xx min. ESMS (C$_{21}$H$_{27}$NO$_2$): calcd. 325.5; obsd. 326.1 [M+H]$^+$.

Example 27

Preparation of Compound (27)

Compound (27) was synthesized in a similar manner to compound (18) using 6-hydroxyquinoline. Retention time (anal. HPLC: 5–75% MeCN/H$_2$O over 4 min)=2.7 min. ESMS (C$_{20}$H$_{22}$N$_2$O$_2$): calcd. 322.4; obsd. 323.0 [M+H]$^+$.

Example 28

Preparation of Compound (28)

Compound (28) was synthesized in a similar manner to compound (18) using 3,5-bis(trifluoromethyl)phenol. Retention time (anal. HPLC: 5–75% MeCN/H$_2$O over 4 min)=3.5 min. ESMS (C$_{19}$H$_{19}$F$_6$NO$_2$): calcd. 407.4; obsd. 408.1 [M+H]$^+$.

Example 29

Preparation of Compound (29)

Compound (29) was synthesized in a similar manner to compound (18) using 2-methoxy-4-cyanophenol. Retention time (anal. HPLC: 5–75% MeCN/H$_2$O over 4 min)=2.7 nm. ESMS (C$_{19}$H$_{22}$N$_2$O$_3$): calcd. 326.4; obsd. 327.1 [M+H]$^+$.

Compounds (30) to (46) were synthesized from compound (M) using a procedure similar to that described in Example 18 by replacing the 2-chlorophenol used therein with the requisite heterocycle or alcohol. The preparation of compounds (30)–(46) is illustrated in Scheme 7.

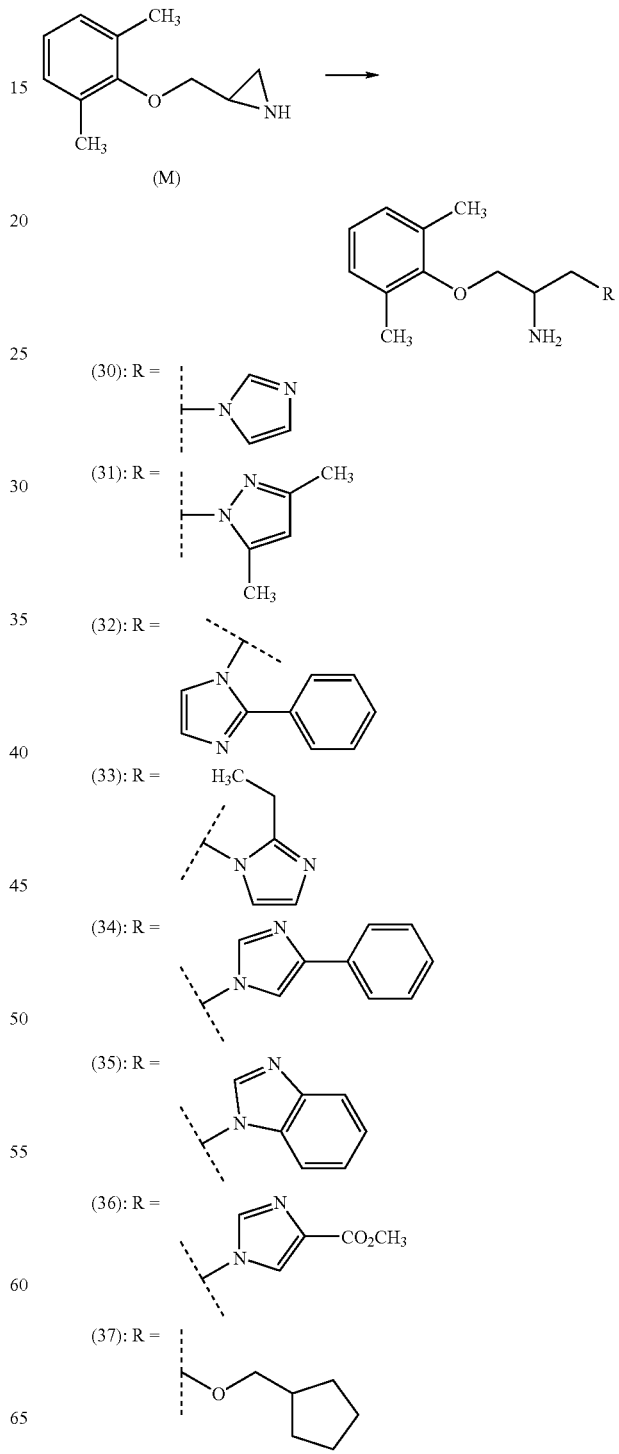

-continued

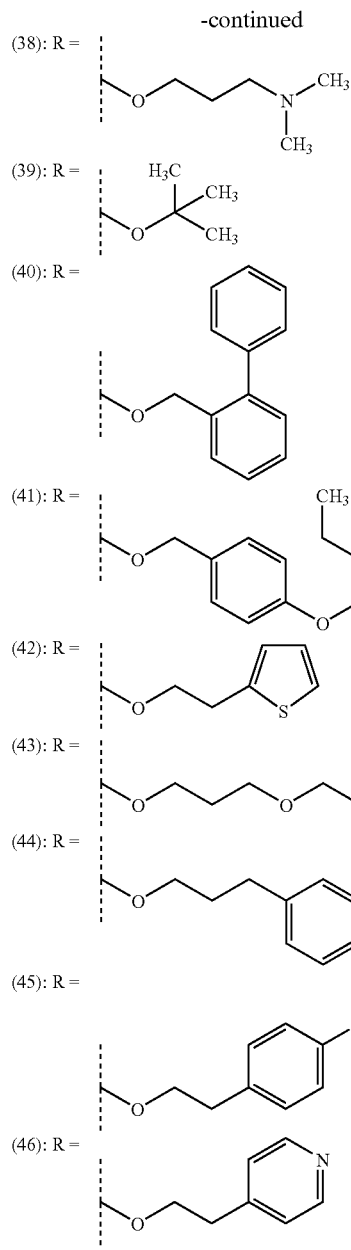

Example 30

Preparation of Compound (30)

Compound (30) was synthesized in a similar manner to compound (18) using imidazole and DMF as a solvent. Retention time (anal. HPLC: 5–75% MeCN/H$_2$O over 4 min)=2.47 min. ESMS (C$_{14}$H, 9N$_3$O): calcd. 245.3; obsd. 245.8 [M]$^+$.

Example 31

Preparation of Compound (31)

Compound (31) was synthesized in a similar manner to compound (18) using 3,5-dimethylpyrazole. Retention time (anal. HPLC: 5–75% MeCN/H$_2$O over 4 min)=2.7 min. ESMS (C$_{16}$H$_{23}$N$_3$O): calcd. 273.3; obsd. 274.0 [M+H]$^+$.

Example 32

Preparation of Compound (32)

Compound (32) was synthesized in a similar manner to compound (18) using 2-phenylimidazole and DMF as a solvent. Retention time (anal. HPLC: 5–75% MeCN/H$_2$O over 4 min)=2.7 min. ESMS (C$_{20}$H$_{23}$N$_3$O): calcd. 321.4; obsd. 322.1 [M+H]$^+$.

Example 33

Preparation of Compound (33)

Compound (33) was synthesized in a similar manner to compound (18) using 2-ethylimidazole. Retention time (anal. HPLC: 5–75% MeCN/H$_2$O over 4 min)=1.9 min. ESMS (C$_{16}$H$_{23}$N$_3$O$_1$): calcd. 273.4; obsd. 274.2 [M+H]$^+$.

Example 34

Preparation of Compound (34)

Compound (34) was synthesized in a similar manner to compound (18) using 4-phenylimidazole and DMF as a solvent. Retention time (anal. HPLC: 5–75% MeCN/H$_2$O over 4 min)=2.5 min. ESMS (C$_{20}$H$_{23}$N$_3$O): calcd. 321.4; obsd. 322.2 [M+H]$^+$.

Example 35

Preparation of Compound (35)

Compound (35) was synthesized in a similar manner to compound (18) using benzimidazole and DMF as a solvent. Retention time (anal. HPLC: 5–75% MeCN/H$_2$O over 4 min)=2.3 min. ESMS (C$_{18}$H$_{21}$N$_3$O): calcd. 295.4; obsd. 296.2 [M+H]$^+$.

Example 36

Preparation of Compound (36)

Compound (36) was synthesized in a similar manner to compound (18) using 4-methylcarboxyimidazole. Retention time (anal. HPLC: 5–75% MeCN/H$_2$O over 4 min)=2.3 min. ESMS (C$_{16}$H$_{21}$N$_3$O$_3$): calcd. 3030.4; obsd. 304.2 [M+H]$^+$.

Example 37

Preparation of Compound (37)

Compound (37) was synthesized in a similar manner to compound (18) using hydroxymethylcyclopentane. Retention time (anal. HPLC: 5–75% MeCN/H$_2$O over 4 min)=3.4 min. ESMS (C$_{17}$H$_{27}$NO$_2$): calcd. 277.4; obsd. 279.1 [M+H]$^+$.

Example 38

Preparation of Compound (38)

Compound (38) was synthesized in a similar manner to compound (18) using 3-N,N-dimethylamino-1-propanol.

Retention time (anal. HPLC: 5–75% MeCN/H$_2$O over 4 min)=1.3 min. ESMS (C$_{16}$H$_{21}$N$_2$O$_2$): calcd. 280.4; obsd. 281.2 [M+H]$^+$.

Example 39

Preparation of Compound (39)

Compound (39) was synthesized in a similar manner to compound (18) using t-butanol. Retention time (anal. HPLC: 5–75% MeCN/H$_2$O over 4 min)=2.3 min. ESMS (C$_{15}$H$_{25}$NO$_2$): calcd. 251.4; obsd. 251.2 [M]$^+$.

Example 40

Preparation of Compound (40)

Compound (40) was synthesized in a similar manner to compound (18) using 1-hydroxymethyl-2-phenylbenzene and DMF as a solvent. Retention time (anal. HPLC: 5–75% MeCN/H$_2$O over 4 min)=3.3 min. ESMS (C$_{24}$H$_{27}$NO$_2$): calcd. 361.5; obsd. 383.2 [M+Na]$^+$.

Example 41

Preparation of Compound (41)

Compound (41) was synthesized in a similar manner to compound (18) using 4-butyloxybenzyl alcohol. Retention time (anal. HPLC: 5–75% MeCN/H$_2$O over 4 min)=3.4 min. ESMS (C$_{22}$H$_{31}$NO$_3$): calcd. 357.5; obsd. 358.2 [M+H]$^+$.

Example 42

Preparation of Compound (42)

Compound (42) was synthesized in a similar manner to compound (18) using 2-(2-hydroxyethyl)thiofuran. Retention time (anal. HPLC: 5–75% MeCN/H$_2$O over 4 min)=2.6 min. ESMS (C$_{17}$H$_{23}$NO$_2$S): calcd. 305.4; obsd. 306.0 [M+H]$^+$.

Example 43

Preparation of Compound (43)

Compound (43) was synthesized in a similar manner to compound (18) using 3-ethoxy-1-propanol. Retention time (anal. HPLC: 5–75% MeCN/H$_2$O over 4 min)=2.7 min. ESMS (C$_{16}$H$_{27}$NO$_3$): calcd. 281.4; obsd. 282.1 [M+H]$^+$.

Example 44

Preparation of Compound (44)

Compound (44) was synthesized in a similar manner to compound (18) using 3-hydroxypropylbenzene. Retention time (anal. HPLC: 5–75% MeCN/H$_2$O over 4 min)=3.4 min. ESMS (C$_{20}$H$_{27}$NO$_2$): calcd. 313.4; obsd. 314.0 [M+H]$^+$.

Example 45

Preparation of Compound (45)

Compound (45) was synthesized in a similar manner to compound (18) using 1-(N,N-dimethylamino)-4-(2-hydroxyethyl)benzene. Retention time (anal. HPLC: 5–75% MeCN/H$_2$O over 4 min)=2.0 min. ESMS (C$_{21}$H$_{31}$N$_2$O$_2$): calcd. 342.5; obsd. 343.2 [M+H]$^+$.

Example 46

Preparation of Compound (46)

Compound (46) was synthesized in a similar manner to compound (18) using 4-(2-hydroxyethyl)pyridine and DMF as a solvent. Retention time (anal. HPLC: 5–75% MeCN/120 over 4 min)=1.7 min. ESMS (C$_{18}$H$_{24}$N$_2$O$_2$): calcd. 300.4; obsd. 301.2 [M+H]$^+$.

Compound (47) to (73) were synthesized from compound (O) according to the procedures described in Scheme 6 with respective nucleophiles (alcohol or heterocycle).

The preparation of compounds (47)–(62) is illustrated in Scheme 8.

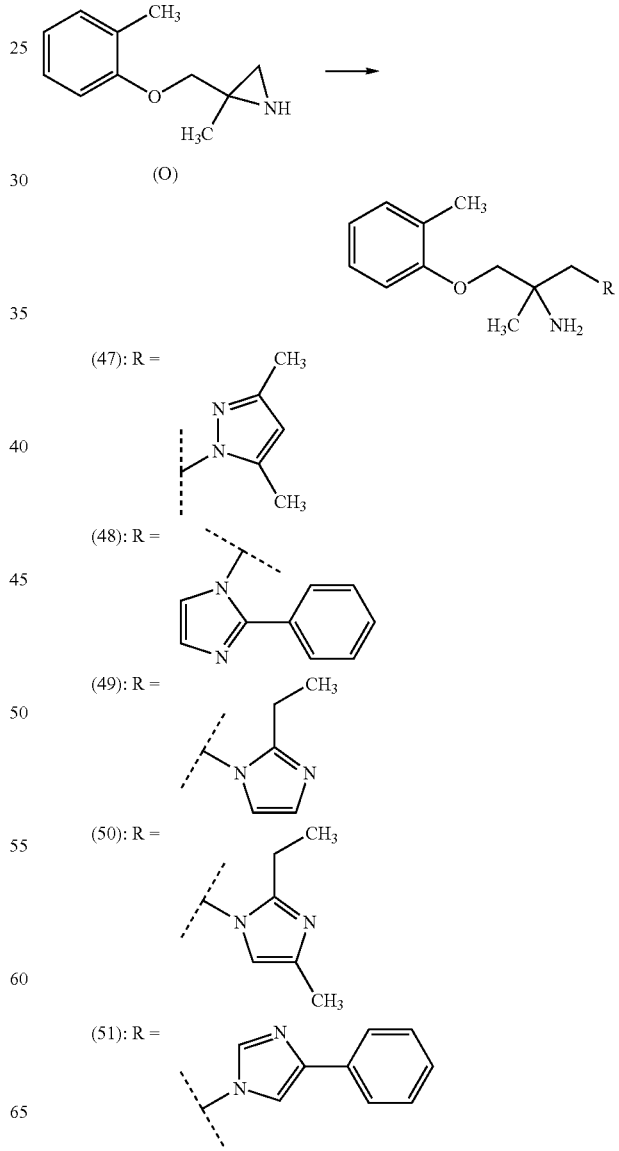

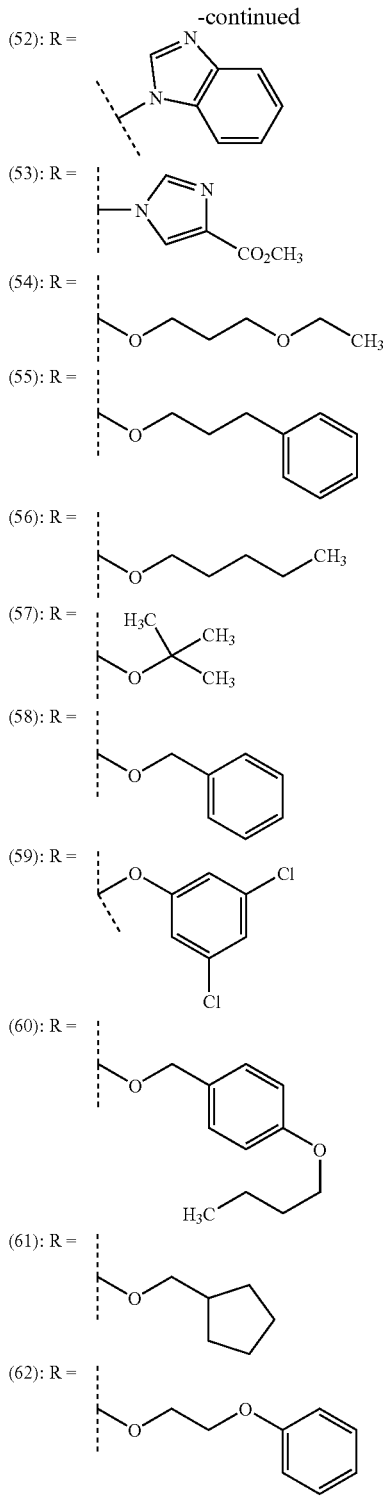

Example 47

Preparation of Compound (47)

A mixture of compound (O) (35.5 mg, 0.2 mmol), 3,5-dimethylpyrazole (19.2 mg, 0.2 mmol), and $BF_3Et_2O$ (28.4 mg, 0.2 mmol) in toluene (0.5 mL) was heated at 90° C. for 24 h. After cooling to rt, the mixture was treated with 5% TFA/50% aqueous acetonitrile (1 mL), and followed by concentration in vacuo. The resulting residue was dissolved in aqueous acetonitrile, and purified by preparative reverse HPLC. The desired product (47) was obtained as TFA salt. Retention time (anal. HPLC: 5–75% $MeCN/H_2O$ over 4 min)=2.5 min. ESMS ($C_{16}H_{23}N_3O$): calcd. 273.4; obsd. 274.1 $[M]^+$.

Example 48

Preparation of Compound (48)

Compound (48) was synthesized in a similar manner to compound (47) using 2-phenylimidazole and DMF as a solvent. Retention time (anal. HPLC: 5–75% $MeCN/H_2O$ over 4 min)=2.2 min. ESMS ($C_{20}H_2N_3O$): calcd. 321.4; obsd. 322.1 $[M+H]^+$.

Example 49

Preparation of Compound (49)

Compound (49) was synthesized in a similar manner to compound (47) using 2-ethylimidazole. Retention time (anal. HPLC: 5–75% $MeCN/H_2O$ over 4 min)=1.9 min. ESMS ($C_{16}H_{23}N_3O$): calcd. 273.4; obsd. 274.2 $[M+H]^+$.

Example 50

Preparation of Compound (50)

Compound (50) was synthesized in a similar manner to compound (47) using 2-ethyl-4-methylmidazole. Retention time (anal. HPLC: 5–75% $MeCN/H_2O$ over 4 min)=1.95 min. ESMS ($C_{17}H_{21}N_3O$): calcd. 287.4; obsd. 288.2 $[M+H]^+$.

Example 51

Preparation of Compound (51)

Compound (51) was synthesized in a similar manner to compound (47) using 4-phenylimidazole and DMF as a solvent. Retention time (anal. HPLC: 5–75% $MeCN/H_2O$ over 4 min)=2.3 min. ESMS ($H_{23}N_3O$): calcd. 321.4; obsd. 322.2 $[M+H]^+$.

Example 52

Preparation of Compound (52)

Compound (52) was synthesized in a similar manner to compound (47) using benzimidazole and DMF as a solvent. Retention time (anal. HPLC: 5–75% $MeCN/H_2O$ over 4 min)=2.0 min. ESMS ($C_{18}H_{21}N_3O$): calcd. 295.4; obsd. 296.2 $[M+H]^+$.

Example 53

Preparation of Compound (53)

Compound (53) was synthesized in a similar manner to compound (47) using 4-methylcarboxyimidazole. Retention time (anal. HPLC: 5–75% $MeCN/H_2O$ over 4 min)=2.0 min. ESMS ($C_{16}H_{21}N_3O_3$): calcd. 3030.4; obsd. 304.2 $[M+H]^+$.

Example 54

Preparation of Compound (54)

Compound (54) was synthesized in a similar manner to compound (47) using 3-ethoxy-1-propanol. Retention time (anal. HPLC: 5–75% MeCN/H$_2$O over 4 min)=2.6 min. ESMS (C$_{16}$H$_{27}$NO$_3$): calcd. 281.4; obsd. 282.1 [M+H]$^+$.

Example 55

Preparation of Compound (55)

Compound (55) was synthesized in a similar manner to compound (47) using 3-hydroxypropylbenzene. Retention time (anal. HPLC: 5–75% MeCN/H$_2$O over 4 min)=3.3 min. ESMS (C$_{20}$H$_{27}$NO$_2$): calcd. 313.4; obsd. 314.0 [M+H]$^+$.

Example 56

Preparation of Compound (56)

Compound (56) was synthesized in a similar manner to compound (47) using n-pentanol. Retention time (anal. HPLC: 5–75% MeCN/H$_2$O over 4 min)=3.1 min. ESMS (C$_{16}$H$_{27}$NO$_2$): calcd. 265.4; obsd. 266.1 [M+H]$^+$.

Example 57

Preparation of Compound (57)

Compound (57) was synthesized in a similar manner to compound (47) using 1-butanol. Retention time (anal. HPLC: 5–75% MeCN/H$_2$O over 4 min)=2.7 min. ESMS (C$_{15}$H$_{25}$NO$_2$): calcd. 251.4; obsd. 251.2 [M]$^+$.

Example 58

Preparation of Compound (58)

Compound (58) was synthesized in a similar manner to compound (47) using benzyl alcohol. Retention time (anal. HPLC: 5–75% MeCN/H$_2$O over 4 min)=2.9 min. ESMS (C$_{18}$H$_{23}$NO$_2$): calcd. 285.4; obsd. 286.1 [M+H]$^+$.

Example 59

Preparation of Compound (59)

Compound (59) was synthesized in a similar manner to compound (47) using 3.5-dichlorophenol. Retention time (anal. HPLC: 5–75% MeCN/H$_2$O over 4 min)=3.4 min. ESMS (C$_{18}$H$_{21}$Cl$_2$NO$_2$): calcd. 354.3; obsd. 354.1 [M]$^+$.

Example 60

Preparation of Compound (60)

Compound (60) was synthesized in a similar manner to compound (47) using 4-butyloxybenzyl alcohol. Retention time (anal. HPLC: 5–75% MeCN/H$_2$O over 4 min)=3.5 min. ESMS (C$_{22}$H$_{31}$NO$_3$): calcd. 357.5; obsd. 358.2 [M+H]$^+$.

Example 61

Preparation of Compound (61)

Compound (61) was synthesized in a similar manner to compound (47) using hydroxymethylcyclopentane. Retention time (anal. HPLC: 5–75% MeCN/H$_2$O over 4 min)=3.1 min. ESMS (C$_{17}$H$_{27}$NO$_2$): calcd. 277.4; obsd. 279.1 [M+H]$^+$.

Example 62

Preparation of Compound (62)

Compound (62) was synthesized in a similar manner to compound (47) using 2-(phenoxy)ethanol. Retention time (anal. HPLC: 5–75% MeCN/H$_2$O over 4 min)=3.0 min. ESMS (C$_{19}$H$_{25}$NO$_3$): calcd. 315.4; obsd. 316.1 [M+H]$^+$.

The preparation of compounds (63)–(73) is illustrated in Scheme 9.

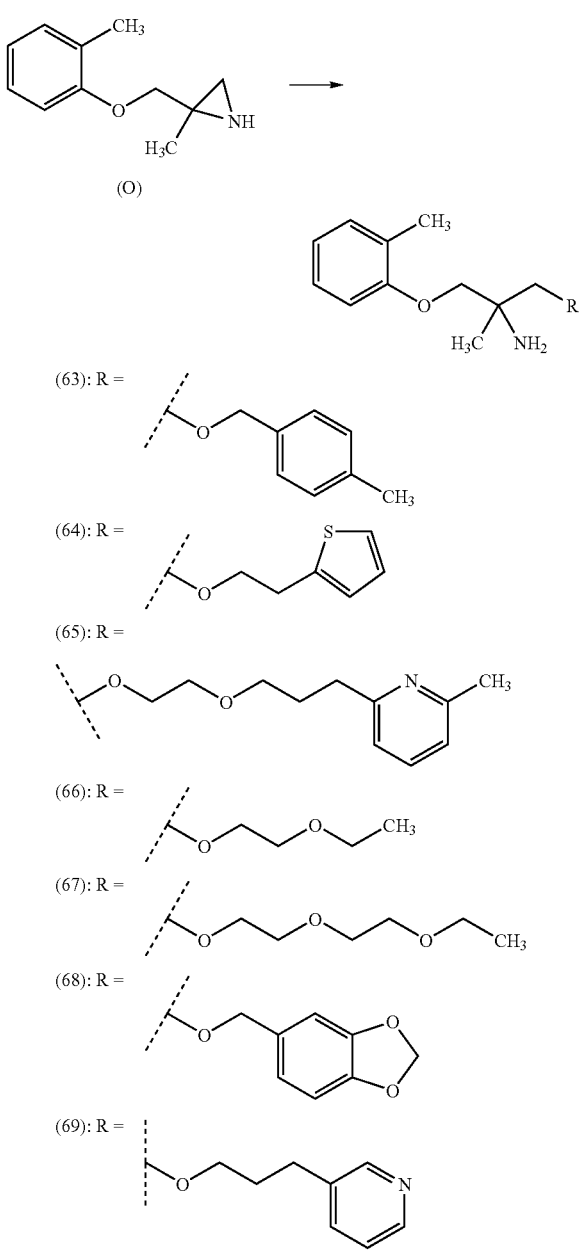

-continued (70): R =

(71): R =

(72): R =

(73): R =

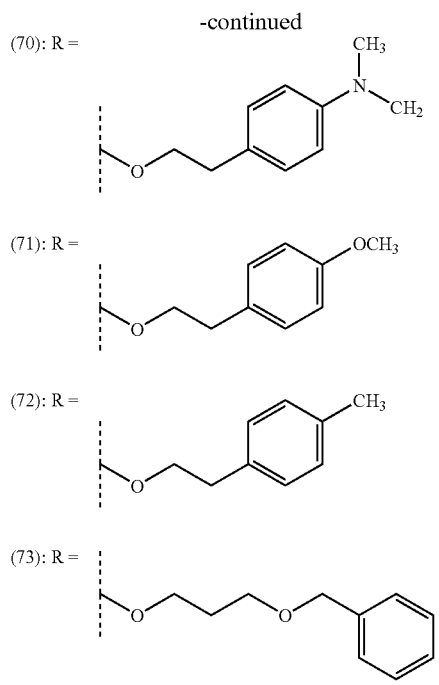

Example 63

Preparation of Compound (63)

Compound (63) was synthesized in a similar manner to compound (47) using 4-methylbenzyl alcohol. Retention time (anal. HPLC: 5–75% MeCN/H$_2$O over 4 min)=3.2 min. ESMS (C$_{19}$H$_{25}$NO$_2$): calcd. 299.4; obsd. 300.2 [M+H]$^+$.

Example 64

Preparation of Compound (64)

Compound (64) was synthesized in a similar manner to compound (47) using 2-(2-hydroxyethyl)thiofuran. Retention time (anal. HPLC: 5–75% MeCN/H$_2$O over 4 min)=3.1 min. ESMS (C$_{17}$H$_{23}$NO$_2$S): calcd. 305.4; obsd. 306.0 [M+H]$^+$.

Example 65

Preparation of Compound (65)

Compound (65) was synthesized in a similar manner to compound (47) using 3-oxa-6-(6-methyl-2-pyridiyl)-1-hexanol and DMF as a solvent Retention time (anal. HPLC: 5–75% MeCN/H$_2$O over 4 min)=3.1 min. ESMS (C$_{22}$H$_{32}$N$_2$O$_3$): calcd. 372.5; obsd. 374.2 [M+H]$^+$.

Example 66

Preparation of Compound (66)

Compound (66) was synthesized in a similar manner to compound (47) using 2-ethoxyethanol. Retention time (anal. HPLC: 5–75% MeCN/H$_2$O over 4 min)=2.5 min. ESMS (C$_{15}$H$_{25}$NO$_3$): calcd. 267.4; obsd. 268.1 [M+H]$^+$.

Example 67

Preparation of Compound (67)

Compound (67) was synthesized in a similar manner to compound (47) using diethylene glycol monoethyl ether. Retention time (anal. HPLC: 5–75% MeCN/H$_2$O over 4 min)=2.5 min. ESMS (C$_{17}$H$_{29}$NO$_4$): calcd. 311.4; obsd. 312.2 [M+H]$^+$.

Example 68

Preparation of Compound (68)

Compound (68) was synthesized in a similar manner to compound (47) using piperonyl alcohol. Retention time (anal. HPLC: 5–75% MeCN/H$_2$O over 4 min)=3.0 min. ESMS (C$_{19}$H$_{23}$NO$_4$): calcd. 329.4; obsd. 330.2 [M+H]$^+$.

Example 69

Preparation of Compound (69)

Compound (69) was synthesized in a similar manner to compound (47) using 3-(3-hydroxypropyl)pyridine and DMF as a solvent. Retention time (anal. HPLC: 5–75% MeCN/H$_2$O over 4 min)=1.6 min. ESMS (C$_{19}$H$_{26}$N$_2$O$_2$): calcd. 314.4; obsd. 315.2 [M+H]$^+$.

Example 70

Preparation of Compound (70)

Compound (70) was synthesized in a similar manner to compound (47) using 1-(N,N-dimethylamino)-4-(2-hydroxyethyl)benzene. Retention time (anal. HPLC: 5–75% MeCN/H$_2$O over 4 min)=2.2 min. ESMS (C$_{21}$H$_{31}$N$_2$O$_2$): calcd. 342.5; obsd. 343.2 [M+H]$^+$.

Example 71

Preparation of Compound (71)

Compound (71) was synthesized in a similar manner to compound (47) using 1-methoxy-4-(2-hydroxyethyl)benzene. Retention time (anal. HPLC: 5–75% MeCN/H$_2$O over 4 min)=3.0 min. ESMS (C$_{20}$H$_{27}$NO$_3$): calcd. 329.4; obsd. 330.1 [M+H]$^+$.

Example 72

Preparation of Compound (72)

Compound (72) was synthesized in a similar manner to compound (47) using 4-methyl-1-(2-hydroxyethyl)benzene. Retention time (anal. HPLC: 5–75% MeCN/H$_2$O over 4 min)=3.2 min. ESMS (C$_{20}$H$_{27}$NO$_2$): calcd. 313.4; obsd. 314.1 [M+H]$^+$.

Example 73

Preparation of Compound (73)

Compound (73) was synthesized in a similar manner to compound (47) using 1,3-dihydroxypropane monobenzyl ether. Retention time (anal. HPLC: 5–75% MeCN/H$_2$O over 4 min)=3.2 min. ESMS (C$_{21}$H$_{29}$NO$_3$): calcd. 343.5; obsd. 344.2 [M+H]$^+$.

The preparation of compounds (74)–(80) is illustrated in Scheme 10.

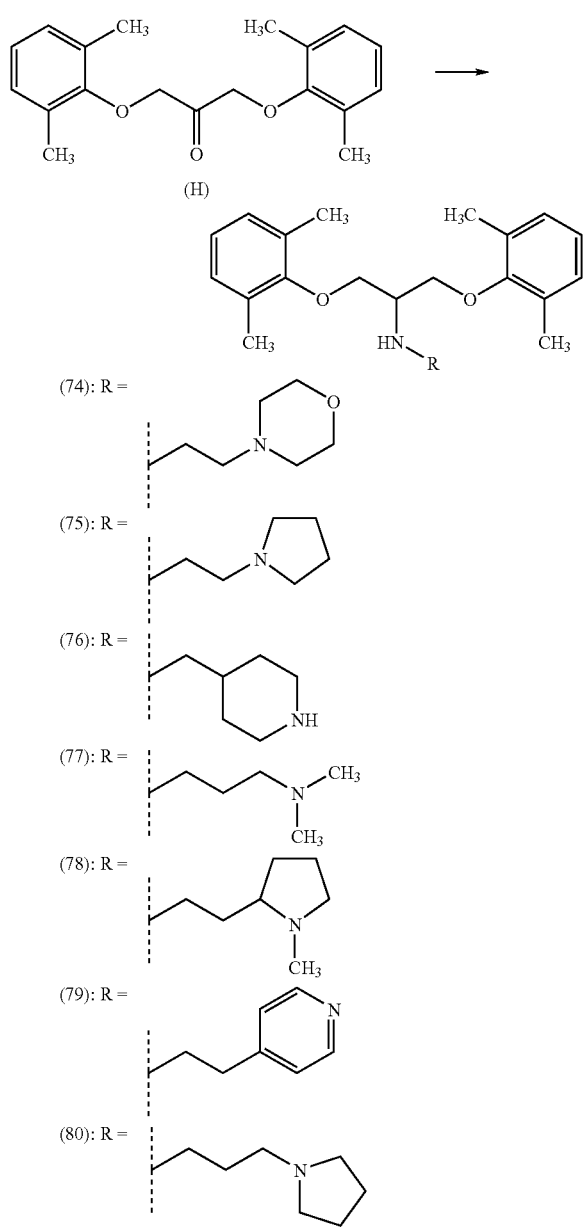

Example 74

Preparation of Compound (74)

To a solution of compound (H) (0.6 g, 2.0 mmol, Example 9 subpart b) and N-(2-aminoethyl)morpholine (0.393 g, 3.0 mmol) in EtOH (50 mL) was added Ti(i-OPr)$_4$ (1.14 g, 4.0 mmol). The mixture was heated at 55° C. for 1 h, and cooled to 0° C. prior to addition of NaCNBH$_3$ (152 mg, 2.42 mmol) and acetic acid (0.5 mL). After stirring for 1 h at the same temperature, the mixture was concentrated in vacuo, yielding oily residue. It was partitioned between EtOAc (100 mL) and 1.0 M NaOH (50 mL). After shaking, the two mixed layers were filtered through Buchner funnel, and allowed to stand in a separatory funnel. The organic layer was separated, dried over MgSO$_4$, and concentrated in vacuo, yielding oily residue. It was dissolved in 50% aqueous acetonitrile (5% TFA), and purified by preparative HPLC. Retention time (anal. HPLC: 10–70% MeCN/H$_2$O over 5 min)=3.3 min. ESMS (C$_{25}$H$_{36}$N$_2$O$_3$): calcd. 412.6; obsd. 413.1 [M+H]$^+$.

Example 75

Preparation of Compound (75)

Compound (75) was synthesized in a similar manner to compound (74) using N-(2-aminoethyl)pyrrolidine. Retention time (anal. HPLC: 10–70% MeCN/H$_2$O over 5 min)= 3.23 min. ESMS (C$_{25}$H$_{36}$N$_2$O$_2$): calcd. 396.6; obsd. 397.2 [M+H]$^+$.

Example 76

Preparation of Compound (76)

Compound (76) was synthesized in a similar manner to compound (74) using 4-aminomethylpiperidine. Retention time (anal. HPLC: 10–70% MeCN/H$_2$O over 5 min)=3.1 min. ESMS (C$_{25}$H$_{36}$N$_2$O$_2$): calcd. 396.6; obsd. 397.2 [M+H]$^+$.

Example 77

Preparation of Compound (77)

Compound (77) was synthesized in a similar manner to compound (74) using N,N-dimethyl-1,3-diaminopropane. Retention time (anal. HPLC: 10–70% MeCN/H$_2$O over 5 min)=3.1 min. ESMS (C$_{24}$H$_{36}$N$_2$O$_2$): calcd. 384.6; obsd. 384.9 [M]$^+$.

Example 78

Preparation of Compound (78)

Compound (78) was synthesized in a similar manner to compound (74) using N-methyl-2(2-aminoethyl)pyrrolidine. Retention time (anal. HPLC: 10–70% MeCN/H$_2$O over 5 min)=3.1 min. ESMS (C$_{26}$H$_{31}$N$_2$O$_2$): calcd. 410.6; obsd. 411.3 [M+H]$^+$.

Example 79

Preparation of Compound (79)

Compound (79) was synthesized in a similar manner to compound (74) using 4-(2-aminoethyl)pyridine. Retention time (anal. HPLC: 10–70% MeCN/H$_2$O over 5 min)=3.1 min. ESMS (C$_{26}$H$_{32}$N$_2$O$_2$): calcd. 404.6; obsd. 405.0 [M+H]$^+$.

Example 80

Preparation of Compound (80)

Compound (80) was synthesized in a similar manner to compound (74) using N-(3-aminopropyl)pyrrolidine. Retention time (anal. HPLC: 10–70% MeCN/H$_2$O over 5 min)= 3.2 min. ESMS (C$_{26}$H 3N$_2$O$_2$): calcd. 410.6; obsd. 411.3 [M+H]$^+$.

The preparation of compounds (81)–(84) is illustrated in Scheme 11.

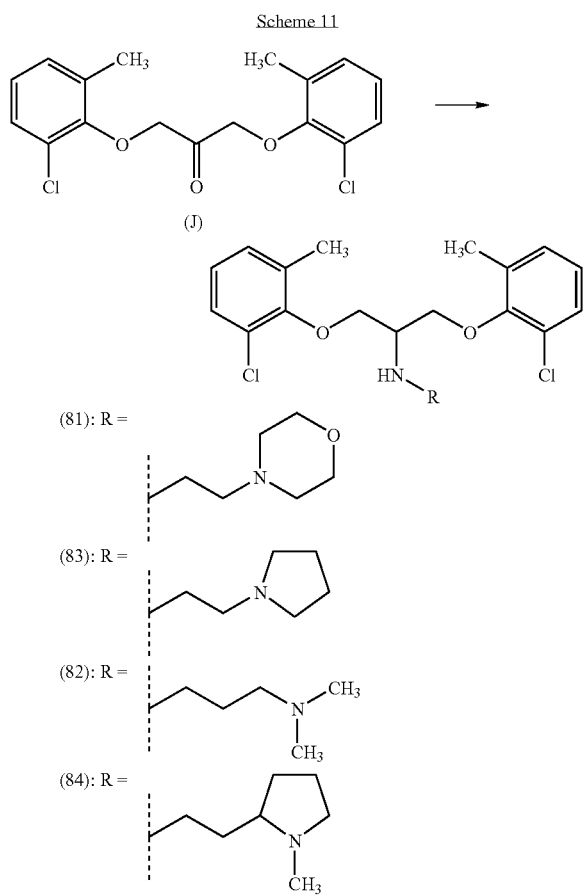

Example 81

Preparation of Compound (81)

A solution of compound (J) (0.5 g, 1.48 mmol) and N-(2-aminoethyl)-morpholine (0.29 g, 2.22 mmol) in toluene (20 mL) was heated at 80° C. for 1 h, and cooled to 0° C. prior to addition of NaCNBH$_3$ (112 mg, 1.78 mmol) and MeOH (10 mL). After stirring for 1 h at the same temperature, the reaction was quenched by adding AcOH (2 mL). The mixture was stirred for 5 min, and concentrated in vacuo, yielding oily residue. It was dissolved in 50% aqueous acetonitrile (5% TFA), and purified by preparative HPLC. The desired product was obtained as TFA salt (240 mg). Retention time (anal. HPLC: 10–70% MeCN/H$_2$O over 5 min)=3.3 min. ESMS (CH$_{30}$Cl$_2$N$_2$O$_3$): calcd. 453.4; obsd. 453.0 [M]$^+$.

The intermediate compound (J) was prepared as follows, as illustrated in Scheme 4.

a. Using a procedure similar to that described in Example 9, sub-part a, except replacing the 2,6-dimethylphenol used therein with 2-chloro-6-methylphenol, compound (F) was prepared. R$_f$=0.91 in hexane/EtOAc (4/1). $^1$H-NMR (CD$_3$OD, 299.96 MHZ): d (ppm) 7.22–7.20 (dd, 2H), 7.18–7.12 (dd, 12H), 7.01–6.98 (t, 2H), 5.49 (s, 2H), 4.6 (s, 4H), 2.31 (s, 6H).

b. Preparation of compound (J). Using a procedure similar to that described in Example 9, sub-part b, except replacing the Compound (D) used therein with Compound (F), Compound (J) was prepared. $^1$H-NMR (CD$_3$OD, 299.96 MHZ): d (ppm) 7.28–7.25 (dd, 2H), 7.2–7.15 (dd, 2H), 7.08–7.0 (t, 2H), 4.88 (s, 4H), 2.33 (s, 6H).

Example 82

Preparation of Compound (82)

Compound (82) was synthesized in a similar manner to compound (81) using N,N-dimethyl-1,3-diaminopropane. Retention time (anal. HPLC: 10–70% MeCN/H$_2$O over 5 min)=3.1 min. ESMS (C$_{22}$H$_{30}$Cl$_2$N$_2$O$_2$): calcd. 425.4; obsd. 425.1 [M]$^+$.

Example 83

Preparation of Compound (83)

Compound (83) was synthesized in a similar manner to compound (81) using N-(2-aminoethyl)pyrrolidine. Retention time (anal. HPLC: 10–70% MeCN/H$_2$O over 5 min)= 3.3 min. ESMS (C$_{23}$H$_{30}$Cl$_2$N$_2$O$_2$): calcd. 437.4; obsd. 437.1 [M]$^+$.

Example 84

Preparation of Compound (84)

Compound (84) was synthesized in a similar manner to compound (81) using N-methyl-2-(2-aminoethyl)pyrrolidine. Retention time (anal. HPLC: 10–70% MeCN/H$_2$O over 5 min)=3.2 min. ESMS (C$_{24}$H$_{32}$Cl$_2$N$_2$O$_2$): calcd. 451.4; obsd. 451.2 [M]$^+$.

The preparation of compounds (85)–(91) is illustrated in Scheme 12.

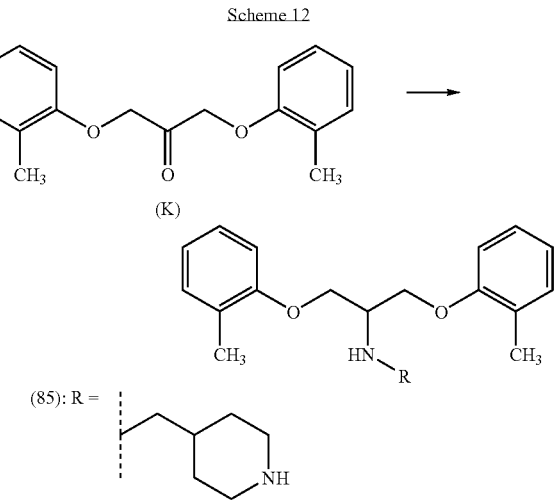

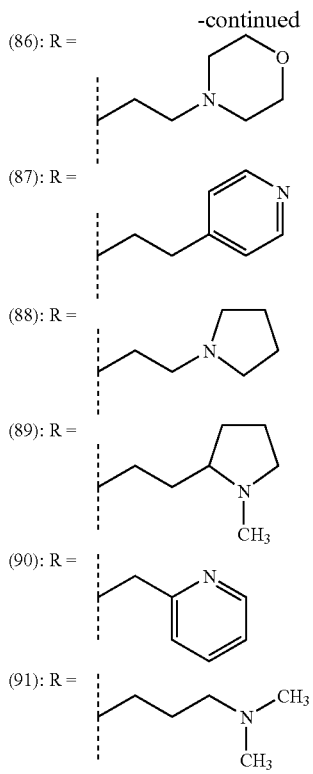

(86): R = [morpholinoethyl]

(87): R = [4-pyridylethyl]

(88): R = [pyrrolidinylethyl]

(89): R = [N-methylpyrrolidin-2-yl-ethyl]

(90): R = [2-pyridylmethyl]

(91): R = [N,N-dimethylaminopropyl]

Example 85

Preparation of Compound (85)

A solution of compound (K) (0.4 g, 1.48 mmol, Example 8, sub-part b) and 4-aminomethylpiperidine (0.24 g, 2.1 mmol) in toluene (20 mL) was heated at 80° C. for 1 h, and cooled to 0° C. prior to addition of NaCNBH$_3$ (105 mg, 1.67 mmol) and MeOH (10 mL). After stirring for 1 h at the same temperature, the reaction was quenched by adding AcOH (2 mL). The mixture was stirred for 5 min, and concentrated in vacuo, yielding oily residue. It was dissolved in 50% aqueous acetonitrile (5% TFA), and purified by preparative HPLC. The desired product was obtained as TFA salt (310 mg). Retention time (anal. HPLC: 10–70% MeCN/H$_2$O over 5 min)=2.95 min. ESMS (C$_{23}$H$_{32}$N$_2$O$_2$): calcd. 368.5; obsd. 368.9 [M]$^+$.

Example 86

Preparation of Compound (86)

Compound (86) was synthesized in a similar manner to compound (85) using N-(2-aminoethyl)morpholine. Retention time (anal. HPLC: 10–70% MeCN/H$_2$O over 5 min)= 3.05 min. ESMS (C$_{23}$H$_{32}$N$_2$O$_3$): calcd. 384.5; obsd. 385.2 [M+H]$^+$.

Example 87

Preparation of Compound (87)

Compound (87) was synthesized in a similar manner to compound (85) using 4-(2-aminoethyl)pyridine. Retention time (anal. HPLC: 10–70% MeCN/H$_2$O over 5 min)=2.95 min. ESMS (C$_{24}$H$_{28}$N$_2$O$_2$): calcd. 376.5; obsd. 377.1 [M+H]$^+$.

Example 88

Preparation of Compound (88)

Compound (88) was synthesized in a similar manner to compound (85) using N-(2-aminoethyl)pyrrolidine. Retention time (anal. HPLC: 10–70% MeCN/H$_2$O over 5 min)= 3.1 min. ESMS (C$_{23}$H$_{32}$N$_2$O$_2$): calcd. 368.5; obsd. 368.9 [α]+.

Example 89

Preparation of Compound (89)

Compound (89) was synthesized in a similar manner to compound (85) using N-methyl-2-(2-aminoethyl)pyrrolidine. Retention time (anal. HPLC: 10–70% MeCN/H$_2$O over 5 min)=3.0 min. ESMS (4H$_{34}$N$_2$O$_2$): calcd. 382.5; obsd. 383.1 [M+H]$^+$.

Example 90

Preparation of Compound (90)

Compound (90) was synthesized in a similar manner to compound (85) using 2-aminomethylpyridine. Retention time (anal. HPLC: 10–70% MeCN/H$_2$O over 5 min)=3.95 min. ESMS (C$_{23}$H$_{26}$N$_2$O$_2$): calcd. 362.5; obsd. 363.2 [M+H]$^+$.

Example 91

Preparation of Compound (91)

Compound (91) was synthesized in a similar manner to compound (85) using N,N-dimethyl-1,3-diaminopropane. Retention time (anal. HPLC: 10–70% MeCN/H$_2$O over 5 min)=2.9 min. ESMS (C$_{22}$H$_{32}$N$_2$O$_2$): calcd. 356.5; obsd. 357.2 [M+H]$^+$.

The preparation of compound (92) is illustrated in Scheme 13.

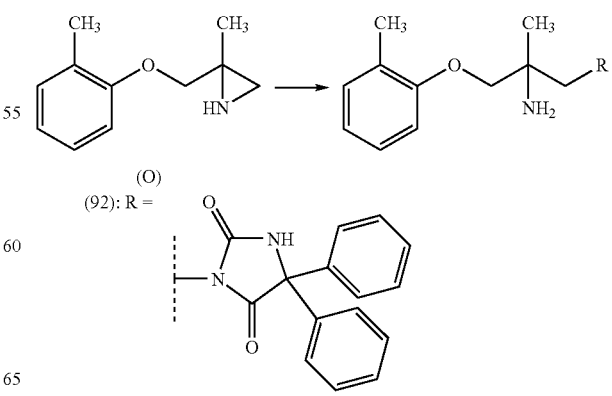

Scheme 13

(92): R = [diphenylhydantoinyl]

Example 92

Preparation of Compound (92)

To a solution of 2-methyl-2-(2'-methylphenyloxymethyl) aziridine (200 mg, 1.13 mmole) and 5,5-diphenylhydantoin (310 mg, 1.13 mmole) in DMF (2 mL) was added conc. HCl (0.04 mL). The reaction mixture was shaken and heated at 70° C. for 12 h. It was worked up by concentration in vacuo, and the residue was purified by preparative reversed-phase HPLC to afford AMI 14762. Retention time (anal. HPLC: 10–70% MeCN/$H_2O$ over 5 min)=3.56 min. ESMS ($C_{26}H_{27}N_3O_3$): calcd. 429.51; obsd. 430.3 $[M+H]^+$.

Example 93

Determination of Sodium Channel Activity

A. Measurement of Sodium Channel Activity in Neonatal Rat Cerebellar Granule Neurons 1. Primary Culture of Rat Cerebellar Granule Neurons:

Primary cultures of cerebellar granule neurons were prepared as described by Gallo et al., *J. Neurochem.*, 54, 1619–25 (1990). Cerebella were dissected from 7 to 8 day-old Sprague-Dawley rats and cut into pieces using a McIlwain tissue chopper. Tissue pieces were incubated with 0.025% trypsin in Hanks Balanced Salt Solution (HBSS) for 10 min at 25° C. Following enzyme treatment, the tissue pieces were resuspended in HBSS buffer containing 1.25 mg/ml soybean trypsin inhibitor and 0.006% DNase and dissociated mechanically by trituration with a fire-polished glass pipette. The cell suspension then was centrifuged at 1000 g for 5 minutes, the supernatant discarded and the pellet resuspended in DMEM/F12 supplemented with 10% fetal bovine serum, 30 mM glucose, 25 mM KCl, 2 mM glutamine, N2 supplement and penicillin (20 U/ml)-streptomycin (20 mg/ml). Cells were plated in 96-well poly-D-lysine-coated black wall-clear bottom culture plates at a concentration of $1-2\times10^5$ cells/well. Cells were maintained at 37° C. in an atmosphere containing 5% $CO_2$. After 18–24 hours, cytosine arabinoside (10 µM final concentration) was added, to inhibit replication of non-neuronal cells.

All experiments were performed using cultures maintained for 4–6 days in vitro (4–6 DIC). In general, the compounds of the invention demonstrated activity in this test.

B. Analysis of Sodium Channel Activity in Rat Cerebellar Granule Neurons Using the Fluorescent Imaging Plate Reader (FLIPR):

To measure sodium channel activity, veratridine-evoked increases in intracellular $CA^{2+}$ ($[Ca^{2+}]_i$) in fluo-3/AM loaded cerebellar granule neurons were monitored, in real-time, using the FLIPR (Molecular Devices, Sunnyvale, Calif.). Cerebellar granule neurons, at 4–6 DIC, were incubated with 4 µM fluo-3/AM in DMEM/F12 medium containing 0.04% pluronic acid for 1–2 hours at 37° C. The neurons then were washed three times with HBSS. The plates were transferred to the FLIPR and the cells incubated for 5 minutes in HBSS, in the absence (control) or presence of antagonist, prior to addition of veratridine (30 µM). Cell fluorescence ($\lambda_{Ex}$=488 nm; $\Delta\lambda_{Em}$=540 nm) was monitored both before and after the addition of veratridine. Peak fluorescence intensity, after veratridine addition, was determined using the FLIPR software. Curve fitting and parameter estimation ($pIC_{50}$) were performed using GraphPad. Stock solutions (10 mM) of compounds were made in 100% DMSO.

In general, compounds of the invention have an $IC_{50}$ of less than 100 µM in this assay, which demonstrates their activity as sodium channel blocking agents. Sodium channel blocking agents have been demonstrated to be clinically effective as local anesthetics, antiarrhythmics and anticonvulsants, and in the treatment of many types of chronic, in particular, neuropathic pain. (See, for example, Hunter J. C. and Loughhead D., Curr. Opin. Invest. Drugs 1999, 1, 72–81.) Sodium channel blockers/modulators also provide neuroprotection and are useful in treatment of migraine (Denyer et al. Drug Discovery Today, 1998, 3, 323–332.) Compounds of the invention, therefore, are expected to have efficacy for treating neuropathic pain or other diseases or conditions associated with sodium channel activity.

Example 94

In Vivo Pain Model

The ability of an agent or a combination of agents to treat pain can be determined using known pharmacological models (for example see Kim, S. H. and Chung, J. M., Pain, 1992, 50, 355–363), or using models that are similar to known models.

Male Sprague-Dawley rats (120–180 g, Harlan, Indianapolis, Ind.) are pre-screened to determine their baseline 50% withdrawal threshold using a set of von Frey filaments. The 50% withdrawal threshold for mechanical stimulation to the hind paw is determined by the up-down method described by Dixon W. J., Ann. Rev. Pharmacol. Toxicol., 1980, 20, 441–462.

Briefly, 8 von Frey filaments with approximately equal logarithmic incremental (0.22) bending forces are chosen (von Frey numbers: 3.65, 3.87, 4.10, 4.31, 4.52, 4.74, 4.92, and 5.16; equivalent to: 0.45, 0.74, 126, 2.04, 3.31, 5.50, 8.32, and 14.45 g). A von Frey filament is applied perpendicularly to the plantar surface with sufficient force to bend it slightly and held for 3–5 seconds. An abrupt withdrawal of the foot during stimulation or immediately after the removal of stimulus is considered a positive response.

Whenever there is a positive or negative response, the next weaker or stronger filament is applied, respectively. The test is continued until six stimuli after the first change in response has been obtained. The pattern of positive and negative responses is converted into a 50% threshold value using the following formula: 50% threshold=10^(X+kd)/10^4, where X=the value of the final von Frey filament used (in log units), k=the tabular value for the pattern of positive/negative responses [obtained from Dixon], and d=the mean difference between stimuli in log units (0.22). In the cases where continuous positive or negative responses are observed all the way out to the end of the stimulus spectrum, values of 0.3 g or 15.0 g are assigned, respectively. For $ED_{50}$ calculations, a linear regression is determined for responses one either side of the 50% reversal and then an approximation is determined based upon the value which intersects the 50% point.

After pre-screening, rats which display a 50% withdrawal threshold greater than 8 g are acceptable for surgery. The spinal nerve ligation (SNL) surgery is carried out as follows. Rats are anesthetized with inhaled Isoflurance and the left L5 and L6 spinal nerves are tightly ligated with 6-0 silk thread. Postoperatively, rats are placed under a heat lamp until motor function returns and then single-housed. At 5–7 days post surgery, rats are re-tested to determine their post-surgery 50% withdrawal threshold. Rats which consistently display (2 or more days) a 50% withdrawal threshold less than 4.5 g are considered acceptable for compound investigation.

Experimental studies typically involve one or more therapeutic compounds, a standard (control), and a vehicle group. Compounds are formulated in saline for injection and pH adjusted with dilute sodium hydroxide. Groups sizes are normally 5 or 6 rats. For routine screening of compounds, a single dose is used (normally 30 mg/kg) and the compound is administered intraperitoneally (typically 2–4 ml/kg). At 1, 3, and 6 hours post administration, the 50% withdrawal threshold is determined by an investigator who is blinded to the treatment groups. If at 6 hours, some prolonged activity is present, i.e., 50% withdrawal thresholds greater than 8 g, then later timepoints may be attempted (normally at 12 and 24 hours). Compounds can also be administered orally to determine oral activity.

Compounds 1–6, 8, 11, and 79 were tested in this model at an intraperitoneal dose of approximately 30 mg/kg. Results for compound 1 demonstrated effectiveness for treating pain; compounds 3, 5, and II showed some activity and compounds 2, 4, 6, 8, and 79 were not active in this model at the tested dose.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (VI):

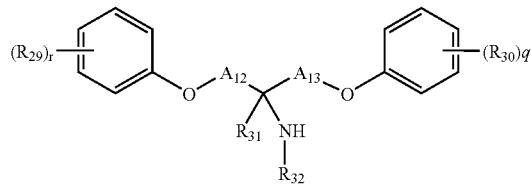

wherein:
   $A_{12}$ and $A_{13}$ are each independently alkylene or substituted alkylene;
   each $R_{29}$ is independently halo, alkyl, substituted alkyl, aryl, heteroaryl, cycloalkyl, substituted cycloalkyl, heterocycle, alkoxy, substituted alkoxy, cycloalkoxy, substituted cycloalkoxy, trifluoromethyl, cyano, nitro, hydroxy, $NR_4R_5$, or $CO_2R_6$;
   each $R_{30}$ is independently halo, alkyl, substituted alkyl, aryl, heteroaryl, cycloalkyl, substituted cycloalkyl, heterocycle, alkoxy, substituted alkoxy, cycloalkoxy, substituted cycloalkoxy, trifluoromethyl, cyano, nitro, hydroxy, $NR_4R_5$, or $CO_2R_6$;
   $R_{31}$ is hydrogen, alkyl, or substituted alkyl;
   $R_{32}$ is 2-morpholinoethyl, 2-(pyrrolidin-1-yl)ethyl 4-piperidinylmethyl, 3-(N,N-dimethylamino)propyl, 2-(1-methyl-pyrrolidin-2-yl)ethyl, 2-(4-pyridyl)ethyl, or 3-(pyrrolidin-1-yl)propyl;

r is 0, 1, 2, 3, 4, or 5;
q is 0, 1, 2, 3, 4, or 5; and
$R_4$–$R_6$ are each independently hydrogen, alkyl, or substituted alkyl;
wherein any aryl of $A_{12}$, $A_{13}$, $R_{29}$–$R_{32}$ and $R_4$–$R_6$ can optionally be substituted with from 1 to 5 substituents $R_g$; wherein each $R_g$ is independently selected from the group consisting of hydroxy, alkyl, substituted alkyl, alkoxy, cycloalkoxy, substituted cycloalkoxy, methanediol, ethanediol, cycloalkyl, substituted alkyl, substituted alkoxy, substituted cycloalkyl, amino, substituted amino, aryl, aryloxy, carboxy, carboxylalkyl, carboxyl(substituted alkyl), cyano, halo, nitro, heteroaryl, heteroaryloxy, heterocyclic, heterocyclooxy, heteroaryl and trihalomethyl;
and wherein any heteroaryl of $A_{12}$; $A_{13}$, $R_{29}$–$R_{32}$ and $R_4$–$R_6$ can be optionally substituted with 1 to 5 substituents $R_h$, wherein each $R_h$ is independently selected from the group consisting of hydroxy, alkyl, alkoxy, substituted alkoxy, cycloalkoxy, substituted cycloalkoxy, substituted alkyl, arylalkyl, heteroarylalkyl, heterocyclealkyl, substituted cycloalkyl, amino, substituted amino, aryl, aryloxy, carboxyl, carboxylalkyl, carboxyl(substituted alkyl), cyano, halo, nitro, heterocyclic, and trihalomethyl.

or a pharmaceutically acceptable salt thereof.

2. The compound of claim 1 wherein $A_{12}$ is methylene or 1,1-ethanediyl and $A_{13}$ is methylene.

3. The compound of claim 1 wherein $R_{31}$ is hydrogen or methyl.

4. The compound of claim 1, which is selected from compounds 74–76, 78–81 and 83–90:

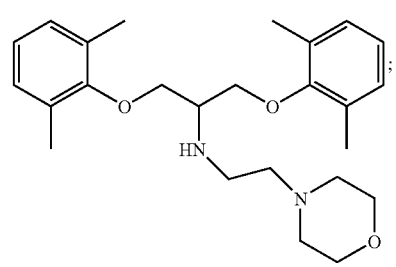

(74)

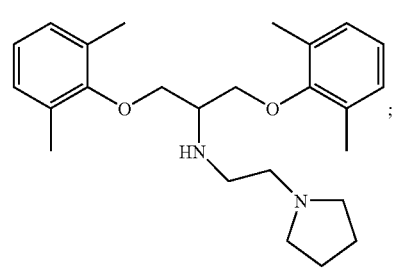

(75)

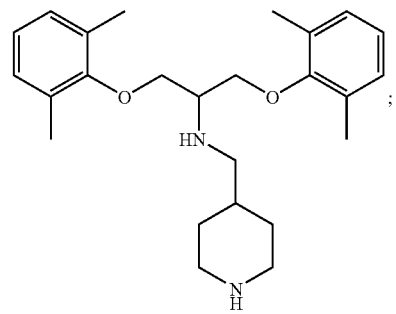

(76)

-continued
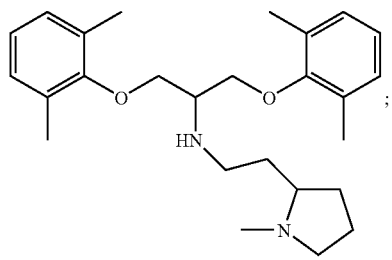 (78)
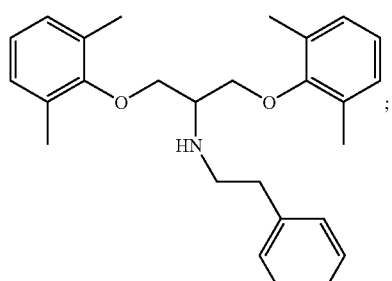 (79)
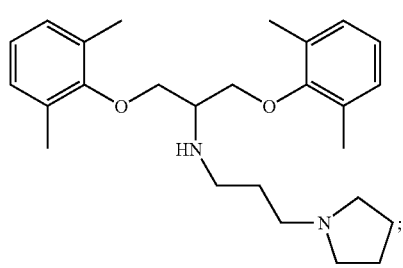 (80)
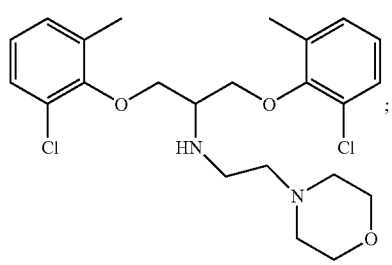 (81)
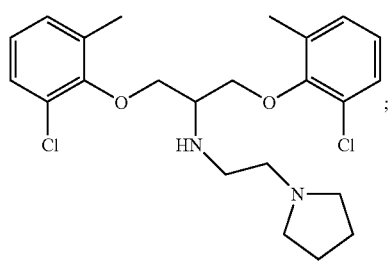 (83)
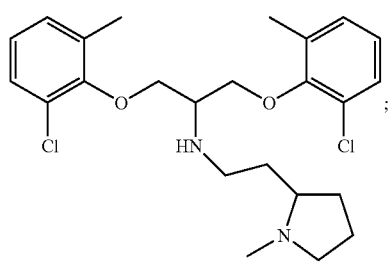 (84)
-continued
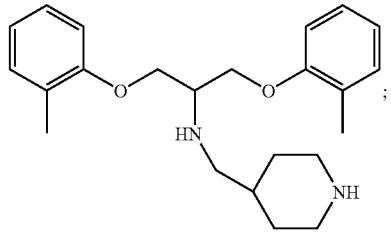 (85)
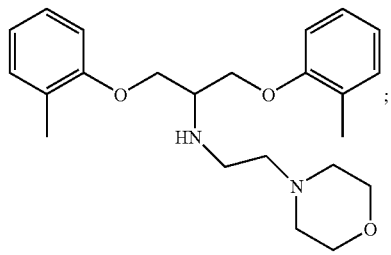 (86)
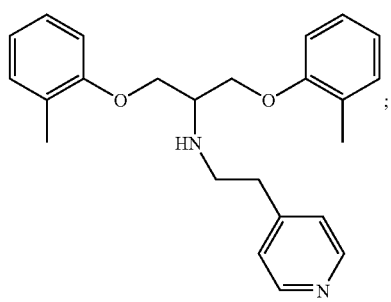 (87)
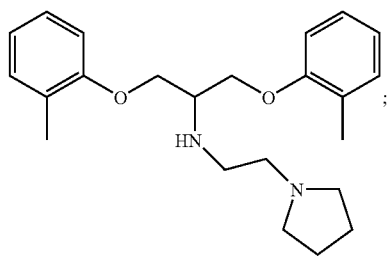 (88)
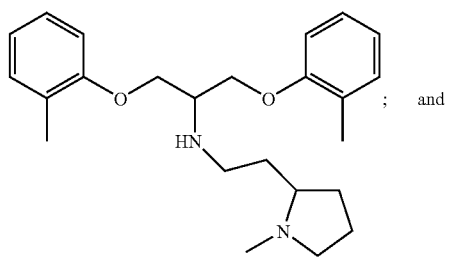 (89) and
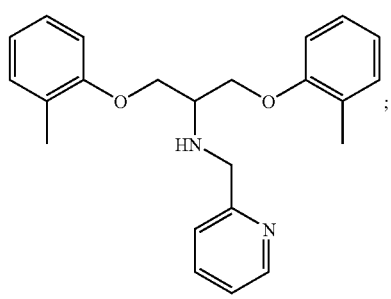 (90)
or a pharmaceutically acceptable salt thereof.

5. A pharmaceutical composition comprising a compound as described in claim 1, and a pharmaceutically acceptable carrier.

6. A method of treating a disease or condition associated with sodium channel activity in a mammal, comprising administering to the mammal, a therapeutically effective amount of a compound as described in claim 1.

7. The method of claim 6 wherein the disease or condition is neuropathic pain.

8. A method of treating a disease or condition associated with sodium channel activity in a mammal, comprising administering to the mammal, a therapeutically effective amount of a pharmaceutical composition of claim 5.

9. The method of claim 8 wherein the disease or condition is neuropathic pain.

10. A compound of claim 1, wherein each $R_{29}$ can independently be alkyl, substituted alkyl, alkoxy, substituted alkoxy, cyano, trifluoromethyl, halo, or $NR_4R_5$.

11. A compound of claim 1, wherein each $R_{30}$ can independently be alkyl, substituted alkyl, alkoxy, substituted alkoxy, cyano, trifluoromethyl, halo, or $NR_4R_5$.

* * * * *

UNITED STATES PATENT AND TRADEMARK OFFICE
CERTIFICATE OF CORRECTION

| | |
|---|---|
| PATENT NO. | : 7,132,422 B2 |
| APPLICATION NO. | : 11/052504 |
| DATED | : November 7, 2006 |
| INVENTOR(S) | : Choi et al. |

It is certified that error appears in the above-identified patent and that said Letters Patent is hereby corrected as shown below:

At Column 63,
line 64, "2-(pyrrolidin-1-yl)ethyl 4-pip-" should read --2-pyrrolidin-1-yl)ethyl, 4-pip-.--.

At Column 64,
line 16, "$A_{12}$;" should read --$A_{12}$,--.

Signed and Sealed this

Twenty-seventh Day of February, 2007

JON W. DUDAS
*Director of the United States Patent and Trademark Office*